United States Patent [19]

Huala et al.

[11] Patent Number: 5,143,846
[45] Date of Patent: Sep. 1, 1992

[54] PROTEASE DEFICIENT BACTERIAL HOSTS

[75] Inventors: Eva Huala, Belmont; Frederick M. Ausubel, Newton, both of Mass.

[73] Assignee: The General Hospital Corporation, Boston, Mass.

[21] Appl. No.: 515,940

[22] Filed: May 2, 1990

Related U.S. Application Data

[63] Continuation-in-part of Ser. No. 169,488, Mar. 17, 1988, Pat. No. 4,970,147.

[51] Int. Cl.⁵ ............ C12N 1/21; C12N 15/31; C12N 15/70
[52] U.S. Cl. ............ 435/252.33; 435/69.1; 435/71.2; 435/91; 435/170; 435/172.1; 435/172.3; 435/252.1; 435/252.3; 435/252.8; 435/320.1; 435/848; 435/852; 435/878; 536/27; 935/6; 935/9; 935/22; 935/29; 935/33; 935/59; 935/60; 935/66
[58] Field of Search ............ 435/69.1, 71.2, 91, 435/170, 172.1, 172.3, 252.1, 252.3, 252.33, 252.8, 320.1, 848, 852, 878, 822; 536/27; 935/6, 9, 22, 29, 33, 49, 59, 60, 61, 66, 72

[56] References Cited

PUBLICATIONS

Beynon et al., 1988, EMBO J., 7(1): 7–14.
Fischer et al., 1987, MGG, 209(3): 621–626.
Ronson et al., 1987, J. Bacteriol., 169(6): 2424–2431.
Huala, E., et al., *J. Bacteriol.* 171: 3354–3365 (1989).
Kohara, Y., et al., *Cell* 50: 495–508 (1987).
Meade, H. M., et al., *J. Bacteriol.* 149: 114–122 (1982).
Ruvkun, G. B., et al., *Nature* 289: 85–88 (1981).
Boyd, D., et al., in *Phosphate Metabolism and Cellular Regulation in Microorganisms*, A. Torriani-Gorini et al., eds., Am. Soc. Microbiol., Washington, D.C., pp. 89–93 (1987).
Parsell, D. A., et al., *J. Biol. Chem.* 264: 7590–7595 (1989).
Chin, D. T. et al., *J. Biol. Chem.* 263: 11718–11728 (1988).
Putney, S. D., et al., *Science* 213: 1497–1501.
Schoemaker, J. M., et al., *J. Bacteriol.* 158: 551–561 (1984).
Fischer, H.-M. et al., *Nucl. Acids Res.* 16: 2207–2224 (1988).

*Primary Examiner*—Richard C. Peet
*Attorney, Agent, or Firm*—Sterne, Kessler, Goldstein & Fox

[57] ABSTRACT

*E. coli* mutants which are capable of expressing cloned proteins in a highly stable manner are described.

9 Claims, 15 Drawing Sheets

PROTEASE DEFICIENT BACTERIAL HOSTS

CROSS REFERENCE TO RELATED APPLICATIONS

This application is a Continuation-in-Part of U.S. Ser. No. 07/169,488, filed Mar. 17, 1988, now U.S. Pat. No. 4,970,147, the contents of which are fully incorporated herein by reference.

FIELD OF THE INVENTION

This invention is in the field of molecular genetics. Specifically, this invention is directed to mutants of *E. coli* which are capable of expressing high levels of heterologous proteins.

BACKGROUND OF THE INVENTION

I. Expression of Foreign Protein in Bacterial Cells

An ability to control or regulate the expression of a cloned homologous or heterologous gene in a host cell is a central requirement of recombinant DNA technology. Recombinant molecules capable of mediating the expression of such genes and methods for employing such molecules are described by Cohen et al., U.S. Pat. Nos. 4,237,224 and 4,468,464 and by Maniatis, T. et al., *Molecular Cloning (A Laboratory Manual)*, 2nd edition, Cold Spring Harbor Laboratory, 1989.

Whether expression of the cloned gene is continuous or modulated, when it is desired to express the gene, it is frequently highly desirable to obtain as much of the protein encoded therein as possible.

The amount of a cloned protein which is recovered from a host reflects an equilibrium between the ability of the host to synthesize the protein and the ability of the host to degrade the protein. Often, bacterial hosts degrade foreign, cloned proteins at rates which are much higher than the degradation rate of a homologous host protein. Thus, it is desirable to identify mechanisms that can minimize such degradation.

II. Nitrogenase Enzymes in *Rhizobium meliloti*

Nitrogen fixation is *Rhizobium meliloti* and other diazotrophs is an inherently oxygen sensitive process. Nitrogenase is protected from oxygen damage within a symbiotic nodule by leghemoglobin, which supplies oxygen to bacteroids within the nodule while maintaining microaerobic conditions. Production of the nitrogenase enzyme in the presence of oxygen is effectively prevented since NifA, the transcriptional activator of the nitrogenase structural genes, is regulated at two levels by oxygen. Transcription of *R. meliloti* nifA is regulated by the environmental sensor/regulator pair fixLJ, which stimulates nifA transcription only under microaerobic conditions (Ditta, G. et al., *J. Bacteriol.* 169:3217-3223 (1987); David, M. et al., Cell 54:671-683 (1988)). In addition, the NifA gene product is itself inactive under aerobic conditions (Fischer. H.-M. et al., *Mol. Gen. Genet.* 209:621-626 (1987); Beynon, J. L. et al., EMBO J. 7:7-14 (1988); Huala, E. et al., *J. Bacteriol.* 171:3354-3365 (1989)). Inactivation of *R. meliloti* NifA under aerobic conditions occurs even when NifA is expressed in *E. coli*, suggesting that either NifA inactivation by oxygen does not require the presence of any host factors, or that such factors are present in both *R. meliloti* and *E. coli*. In contrast, NifA from the free-living diazotroph *Klebsiella pneumoniae* is oxygen sensitive only in the presence of nifL, which is cotranscribed with NifA in *K. pneumoniae* but for which no homologue has been found in any symbiotic nitrogen-fixing species. How the nifL product modulates NifA activity in *K. pneumoniae* in response to the oxygen level remains unclear.

Previous work on *R. meliloti* NifA demonstrated that small changes in the amino acid sequence of the amino terminus can have a drastic effect on the level of NifA accumulation when expressed in *E. coli* (Huala, E. et al., *J. Bacterial.* 171:3354-3365 (1989)). NifA translated from the first in-frame AUG codon (NifA-AUG1) accumulates to very low levels when cells are grown aerobically, and reaches slightly higher levels when grown under 1% oxygen. By contrast, several variant NifAs with altered amino terminal sequences accumulate to very high levels in *E. coli* during aerobic or microaerobic growth, most like due to differences in stability (Huala, E. et al., *J. Bacteriol.* 171:3354-3365 (1989)). It appears likely that this difference in stability is mediated by a factor present in *E. coli* but absent in *R. meliloti*, since in *R. meliloti* no difference in accumulation between different forms of NifA is observed. However, factors in *E. coli* which cause the rapid decrease in NifA-AUG1 transcriptional activity in the presence of oxygen have not been identified. If such factors could be identified or inactivated, *E. coli* hosts may be capable of maintaining increased levels of expressed protein in a highly stable manner.

SUMMARY OF THE INVENTION

Recognizing the importance that elucidation of the pathway in *E. coli* which causes the rapid decrease in NifA-AUG1 transcriptional activity in the presence of oxygen would provide, the inventor set out to identify factors in *E. coli* which mediate the decrease in NifA activity at high oxygen, either by decreasing NifA accumulation or by contributing to the inactivation of NifA. The inventor performed a Tn5 mutagenesis of *E. coli* and isolated mutants with increased NifA-AUG1 activity during aerobic growth. These studies have cumulated in the identification of mutant *E. coli* host cells which have the capability of expressing cloned proteins in a highly stable manner.

Therefore, it is an object of the invention to provide bacterial hosts which express foreign proteins in a highly stable manner.

It is a further object of the invention to provide methods of creating and identifying such hosts.

DESCRIPTION OF THE PREFERRED EMBODIMENTS

I. Definitions

Figure 1A:
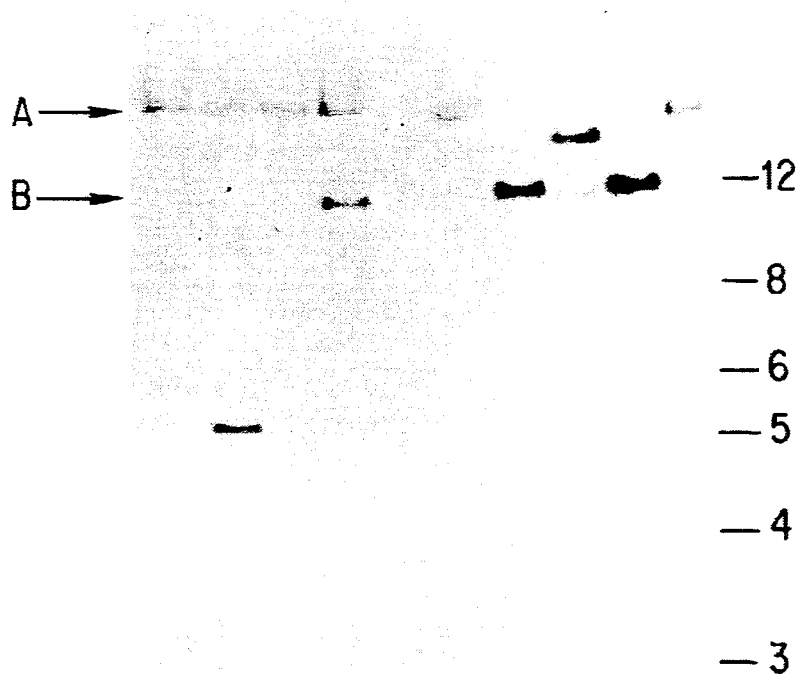
FIG. 1 (parts A and B). Groups of Tn5 insertions into three classes. Southern blot or EcoRI restricted DNA from strains LC2-LC25, probed with Tn5. Molecular weights are shown in kilobases on the right. Arrows indicate insertions in snoA (A), snoB (B), and snoC (C).

In the description that follows, a number of terms used in recombinant DNA (rDNA) technology extensively utilized. In order to provide a clear and consistent understanding of the specification and claims, including the scope to be given such terms, the following definitions are provided.

Gene. A DNA sequence containing a template for a RNA polymerase. The RNA transcribed from a gene may or may not code for protein, RNA that codes for a protein is termed messenger RNA (mRNA).

A "complementary DNA" or "cDNA" gene includes recombinant genes synthesized by reverse transcription of mRNA.

Cloning vehicle. A plasmid or phase DNA or other DNA sequence which is able to replicate autonomously in a host cell, and which is characterized by one or a small number of endonuclease recognition sites at which such DNA sequences may be cut in a determinable fashion without loss of an essential biological function of the vehicle, and into which DNA may be spliced in order to bring about its replication and cloning. The cloning vehicle may further contain a marker suitable for use in the identification of cells transformed with the cloning vehicle. Markers, for example, are tetracycline, kanamycin, or ampicillin resistance. The word "vector" is sometimes used for "cloning vehicle."

Expression vehicle. A vehicle or vector similar to a cloning vehicle but which is capable of expressing a gene which has been cloned into it, after transformation into a host. The cloned gene is usually placed under the control of (i.e., operably linked to) certain control sequences such as promoter sequences. Expression control sequences will vary depending on whether the vector is designed to express the operably linked gene in a continuous manner or a regulated manner and may additionally contain transcriptional elements such as termination sequences, sequences which enhance the translation of mRNA, and sequence which promote secretion of the protein.

II. Genetic Engineering of the Mutants of the Invention

The invention provides stable E. coli host cell lines which are capable of replicating and continuously growing in suitable culture medium and environmental conditions. Additionally, these host cells contain mutations which inactivate proteolytic pathways and allow for the unexpectedly high accumulation of foreign proteins. Additionally, these cells are capable of serving as a source for the purification and cloning of the mutated genes which are responsible for the inactivated proteolytic pathways. Additionally, these cells are capable of serving as a model system to assay for the presence of factors and other agents, including additional mutations, which may reverse or enhance the inherent ability of these cells to express cloned proteins in a highly stable manner.

A deposit of the cells lines of the invention has been made with the American Type Culture Collection, 12303 Parklawn Drive, Rockville, MD 20852, USA on May 1, 1990. Host cell LC24, which contains a snoC mutation, is assigned the accession number ATCC 55040. Host cell HA63, which contains a lon and snoB double mutation, is assigned the accession number ATCC 55039.

The present invention relates to a bacterial host cell which contains a mutation in its native snoC gene, or in the regulatory elements therefore. This mutation results in a host cell which is defective in proteolytic pathways used to degrade foreign proteins, and which, as a result of such mutation, accumulates surprising amounts of such foreign proteins.

The present invention further relates to a bacterial host cell which is a double mutant and contains a mutation in its native lon gene and in its native snoB gene. This double mutation also results in a host cell which is defective in proteolytic pathways used to degrade foreign proteins, and which, as a result of such mutations, accumulates surprising amounts of such foreign proteins.

Two classes of $E.$ $coli$ sno (stability of NifA is oxygen) mutants were identified by the method of the invention as providing for the surprising stability of foreign proteins in $E.$ $coli$ host cells. The first class are double mutants in the $E.$ $coli$ snoB lon loci. The second class are single mutants in the $E.$ $coli$ snoC locus. Both snoB lon double mutants and snoC single mutants result in host cells which posses a decreased ability to degrade foreign proteins.

The mutants of the invention may be identified by a selection scheme which makes use of a recombinant construct which contains a NifA-regulated promoter ($R.$ $meliloti$ nifH) fused to a reporter gene, lacZ. The host strain, $E.$ $coli$ strain MC1061, which has been transformed with this construct grows very poorly on lactose minimal medium in the absence on active NifA. Therefore, when NifA is not expressed, or is otherwise inactivated or not present in the host, the host grows every poorly, on lactose minimal medium. By very poor growth is meant that wild type MC1061 produces barely visible colonies after 84 hours of growth at 28° C.

To create the mutants of the invention, $E.$ $coli$ strain MC1061, carrying a gene for kanamycin resistance, the lacZ-NifA expression plasmid pEH32, and the nifH-lacZ reporter plasmid pMB210, may be mutagenized, for example, with Tn5, and plated on lactose minimal plates. Mutants with an increased level of NifA activity, resulting in an increased ability to activate expression of the nifH-lacZ fusion, appear as larger colonies against a background of microcolonies. Large kanamycin resistant colonies may be isolated by restreaking on lactose minimal medium and their large size verified by plating each one on lactose minimal medium and comparing them to wild type MC1061 carrying pEH32 and pMB210. The absence of a Tn5 insertion on the plasmids carried by the MC1061 mutants may be verified by isolating plasmid DNA from each mutant and transforming $E.$ $coli$ MC1061. If no kanamycin resistant colonies result, then the Tn5 insertions are located on the chromosome.

To identify the site of the mutation (here the site of Tn5 insertion), chromosomal DNA from each mutant strain may be extracted by techniques known in the art, and digested with restriction enzymes, and analyzed on a Southern blot using a probe. For mutants may be Tn5 mutation, a Tn5 probe is used. If the hosts have been chemically mutagenized, the location of the mutation can be determined by chemical sequencing.

Using Tn5 mutation as described above, mutations were found to occur in three different EcoR1 fragments of the host's genome. These were designated as snoA mutants (group 1), snoB mutants (group 2), or snoC (group 3) mutants. In addition, as described below, in some cases double mutations were made.

The approximate genetic locations of the mutations may be determined by Hfr mapping. The snoA mutation of the invention is between 6 and 13 min, the snoB mutation of the invention is between 23 and 30 min, and the snoC mutation of the invention is between 51 and 61 min on the genetic map of Bachmann, B. J., in $Escherischia$ $coli$ and $Salmonella$ $typhimurium$, F. C. Neidheardt, ed., vol. II, (1987), Am. Soc. Microbiology, Washington, pp. 807–876.

To examine the oxygen stability of the expressed protein, the sno mutants which contain plasmids pEH32 (NifA-AUB1) and pMB210 (nifH-lacZ) may be grown in LB medium under a continuous stream of either 1% or 21% oxygen for 16 hours and assayed for $\beta$-galactosidase activity from the nifH-lacZ reporter fusion. When grown at 21% oxygen, the mutants of the invention show levels of $\beta$-galactosidase activity about ten fold higher than wild type MC1061 containing pEH32 and pMB210. At 1% oxygen, snoA and snoC mutants show slightly elevated levels of $\beta$-galactosidase activity relative to MC1061, while snoB mutants show no relative increase in $\beta$-galactosidase activity.

The lon::Tn10 insertion from Mph82 may be transduced into single mutant hosts such as LC23 and LC24 to create double mutants hosts strains (strains HA63 (lon snB) and HA64 (lon snoC), respectively). These double mutants may also be transformed with pEH32 or pEHΔR1 and the accumulation of NifA was observed.

To determine the sequence and identity of the mutations, the Tn5 insertion and surrounding DNA may be subcloned from each mutant. The mutation which results in the snoA phenotype in LC12 is about 55 kb from proC, within the lon gene which encodes the protease La. The mutation which results in the snoB phenotype of host LC23 is located approximately 160 base pairs downstream of the termination codon for alaS, which encodes alanyl tRNA synthetase. The mutation which results in the snoC phenotype of host LC24 is located approximately 10 kilobases away from nirR (29.4 min) in the direction of rac.

The ability of a mutant to express a foreign protein in a stable manner may be determined by assaying levels of the protein in the host cells, either immunologically with antibodies to the protein.

III. Genetic Engineering of Proteins to be Expressed in the Mutants of the Invention The process for genetically engineering protein sequences, according to the invention, is facilitated through the cloning of genetic sequences which are capable of encoding the desired protein and through the expression of such genetic sequences. As used herein, the term "genetic sequences" is intended to refer to a nucleic acid molecule (preferably DNA). Genetic sequences which are capable of encoding the desired protein are derived from variety of sources. These sources include genomic DNA, cDNA, synthetic DNA, and combinations thereof.

If genomic DNA is utilized as the source of the coding sequence, it may or may not include naturally occurring introns. Moreover, such genomic DNA may be obtained in association with the 5' promoter region of the and/or with the 3' transcriptional termination region. To the extent that a host cell can recognize the transcriptional and/or translational regulatory signals associated with the expression of the desired mRNA and protein, then the 5' and/or 3' nontranscribed regions of the native gene, and/or, the 5' and/or 3' non-translated regions of the mRNA, may be retained and employed for transcriptional and translational regulation.

Genomic DNA can be extracted purified from any cell by means well known in the art (for example, see *Guide to Molecular Cloning Techniques*, S. L. Berger et al., eds., Academic Press (1987)).

Alternatively, the mRNA for the desired protein can be isolated from any cell which produces or expresses the protein, and used to produce cDNA by means well known in the art (for example, see *Guide to Molecular Cloning Techniques*, S. L. Berger et al., eds., Academic Press (1987)). Preferably, the mRNA preparation used will be enriched in mRNA coding for the desired protein, either naturally, by isolation from a cells which are producing large amounts of the protein, or in vitro, by techniques commonly used to enrich mRNA preparations for specific sequences, such as sucrose gradient centrifugation, or both.

For cloning into a vector, such suitable DNA preparations (either genomic DNA or cDNA) are randomly sheared or enzymatically cleaved, respectively, and ligated into appropriate vectors to form a recombinant gene (either genomic or cDNA) library.

A DNA sequence encoding a desired protein may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., supra, and are well known in the art.

Recombinant libraries may be screened and a clone to the desired protein identified by any means which specifically selects for nucleic acid specific to such protein, such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immuno-precipitated of the translated protein product produced by the host containing the clone.

Oligonucleotide probes specific for a protein which can be used to identify clones to this protein and can be designed from knowledge of the amino acid sequence of the protein. Because the genetic code is degenerate, more than one codon may be used to encode a particular amino acid (Watson, J. D., In: *Molecular Biology of the Gene*, 3rd Ed., W. A. Benjamin, Inc., Menlo Park, CA (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oliginoculeotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., in: *Molecular Biology of the Gene*, 3rd Ed., W. A. Benjamin, Inc., Menlo Park CA (1977)), one or more different oligonucleotides can be identified from the amino acid sequence, each of which would be capable of encoding the desired protein. The probability that a particular oligonucleotide will, in fact, constitute the actual protein's sequence can be estimated by considering abnormal base pairing relationship and the frequency with which a particular codon is actually used (to encode a particular amino acid) in prokaryotic cells. Such "codon usage rules" are disclosed by Lathe, R., et al., *J. Molec. Biol.* 183:1–12 (1985). Using the "codon usage rules" of Lathe, a single oligonucleotide sequence, or a set of oligonucleotide sequences, that contain a theoretical "most probable" nucleotide sequence capable of encoding the protein is identified.

The suitable oligonucleotide, or set of oligonucleotides, which is capable of encoding a fragment of the protein's gene (or which is complementary to such an oligonucleotide, or set of oligonucleotides) may be synthesized by means well known in the art (see, for example, *Synthesis and Application of DNA and RNA*, S. A. Narang, ed., 1987, Academic Press, San Diego, CA) and employed as a probe to identify and isolate the cloned protein's gene by techniques known in the art. Techniques of nucleic acid hybridization and clone identification are disclosed by Maniatis, T., et al. (in: *Molecular Cloning, A Laboratory Manual*, 2nd edition, Cold Spring Harbor Laboratories, Cold Spring Harbor, NY (1989)), and by Hames, B. D., et al. (in: *Nucleic Acid Hybridization, A Practical Approach*, IRL Press, Washington, DC (1985)). Those members of the above-described gene library which are found to be capable of such hybridization are then analyzed to determine the extent and nature of the protein encoding sequence which they contain.

To facilitate the detection of the desired DNA encoding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby, P. J. W., et al., *J. Mol. Biol.* 113237 (1977) and by T4 DNA polymerase replacement synthesis as described in, for example, Deen, K. C., et al., *Anal. Biochem.* 135:456 (1983).

Alternatively, polynucleotides are also useful as nucleic acid hybridization probes when labeled with a non-radioactive marker such as biotin, an enzyme or a fluorescent group. See, for example, Leary, J. J., et al., *Proc. Natl. Acad. Sci.* USA 80:4045 (1983); Renz, M., et al., *Nucl. Acids Res.* 12:3435 (1984); and Renz, M., *EMBO J.* 6:817 (1983).

Thus, in summary, the actual identification of protein sequences permits the identification of a theoretical "most probable" DNA sequence, or a set of such sequences, capable of encoding such a protein, By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing the sequences encoding such protein.

In an alternative way of cloning the protein, a recombinant library is prepared using an expression vector, by cloning DNA or, more preferably cDNA prepared from a cell capable of expressing the protein, into an expression vector. The library is then screened for members which express the desired protein, for example, by screening the library with antibodies to the protein.

The above discussed methods are, therefore, capable of identifying genetic sequences which are capable of encoding a protein or fragments of this protein. In order to further characterize such genetic sequences, and, in order to produce the recombinant protein, it is desirable to express the proteins which these sequences encode. Such expression identifies those clones which express proteins possessing characteristics of the desired protein. Such characteristics may include the ability to specifically bind antibodies directed to the protein, the ability to elicit the production of antibody which are capable of binding to the protein, and the ability to provide a function unique to that protein to a recipient cell, among others.

III. Expression of a Protein Cloned in a Host of the Invention

To express a cloned protein which is foreign (heterologous) to the host of the invention, or homologous to the host, transcriptional and translational signals recognizable by the host are necessary. The cloned protein encoding sequences, obtained through the methods described above, and preferably in a double-stranded form, may be operably linked to sequence controlling transcriptional expression in an expression vector, and introduced into the host cell, to produce the recombinant protein.

A nucleic acid molecule, such as DNA, is said to be "capable of expressing" a polypeptide if it contains expression control sequences which contain transcriptional regulatory information and such sequences are "operably linked" to the nucleotide sequence which encode the protein.

An operable linkage is a linkage in which a sequence is connected to a regulatory sequence (or sequences) in such a way as to place expression of the sequence under the influence or control of the regulatory sequence. Two DNA sequences (such as a sequence encoding a protein and a promoter region sequence linked to the 5' end of the encoding sequence) are said to be operably linked if induction of promoter function results in the transcription of the protein's encoding sequence mRNA and if the nature of the linkage between the two DNA sequences does not (1) result in the introduction of a frame-shift mutation, (2) interfere with the ability of the expression regulatory sequences to direct the synthesis of the protein's RNA, or (3) interfere with the ability of the DNA template to be transcribed by the promoter region sequence. Thus, a promoter region would be operably linked to a DNA sequence if the promoter were capable of effecting transcription of that DNA sequence.

The precise nature of the regulatory regions needed for gene expression may vary, but may in general include, 5' non-transcribing and non-coding sequences involved with initiation of transcription, such as the TATA box, capping sequence, CAAT sequence, and the like. Especially, such 5' non-transcribing control sequences will include a region which contains a promoter for transcriptional control of the operably linked gene.

Transcriptional initiation regulatory signals can be selected which allow for repression or activation, so that expression of the operably linked genes can be modulated. Where the native expression control sequences signals do not function satisfactorily host cell, then sequences functional in the host cell may be substituted.

In a preferred embodiment, genetically stable host transformants may be constructed with vector systems, or transformation systems, whereby the desired protein's DNA is integrated into the host chromosome. Such integration may occur de novo within the cell or, in a most preferred embodiment, be assisted by transformation with a vector which functionally inserts itself into the host chromosome, for example, transposons or other DNA elements which promote integration of DNA sequences in chromosomes.

Cells which have been transformed with DNA are selected by also introducing one or more markers which allow for selection of host cells which contains the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by cotransfection.

In another embodiment, the introduced sequence is incorporated into a plasmid or viral vector capable of autonomous replication in the recipient host. Any of a wide variety of vectors may be employed for this purpose.

Factors of importance in selecting a particular plasmid or viral vector include: the ease with which recipient cells that contain the vector maybe recognized and selected from those recipient cells which do not contain the vector; the number of copes of the vector which are desired in a particular host; and whether it is desirable to be able to "shuttle" the vector between host cells of different species.

Once the vector or DNA sequence containing the construct(s) is prepared for expression, the DNA construct(s) is introduced into an appropriate host cell (which is then said to be "transformed") by any of a variety of suitable means. After the introduction of the vector, recipient transformed cells are grown in a selective medium, which selects for the growth of vector-containing cells. Expression of the cloned gene sequence(s) results in the production of the desired protein. This expression can take place in a continuous manner in the transformed cells, or in a controlled manner.

The expressed protein is isolated and purified from the host cell of the invention in accordance with conventional conditions, such as extraction, precipitation, chromatography, affinity chromatography, electrophoresis, or the like.

The following examples further describe the materials and methods used in carrying out the invention. The examples are not intended to limit the invention in any manner.

EXAMPLES

MATERIALS AND METHODS

Radioisotopes, bacterial strains and media. All radioisotopes were purchased from New England Nuclear. Bacterial strains and plasmids used in this study are listed in Table 1. LB medium (Meade, H. M. et al., *J. Bacteriol.* 149:114-122 (1982)), M9 minimal medium and M63 minimal medium (Miller, J. H., Experiments in Molecular Genetics, Cold Spring Harbor Laboratory Press, Cold Spring Harbor, New York (1972)) have been previously described.

Isolation of Tn5 mutants. MC1061 containing plasmids pEH32 and pMB210 was infected with λb221 rex::Tn5 cI857 $O_{am8}$ $P_{am28}$ (Berg. D., Insertion and excision of the transposable kanamycin resistance determinant Tn5, p. 205-212, in A. I. Bukhari. J. A. Shapiro, and S. L. Anhya (ed.), DNA insertion elements, plasmids, and episome, Cold Spring Harbor Laboratory, Cold Spring Harbor, New York (1977); Ruvkun, G. B. of al., *Nature* 289:85-88 (1981)). Eight ml of cells, grown in LB medium to a density of $1 \times 10^9$ cells per ml, were infected at a multiplicity of infection of 0.1, incubated at 32° C. for 4 hours, and plated on M9 minimal medium supplemented with 0.4% lactose as the sole carbon source and 25 μg/ml kanamycin. Extremely small kanamycin resistant colonies were visible under a dissecting microscope after 84 hours of incubation at 28° C. (a temperature which permits high NifA activity) at a density of about 12,000 colonies on each of 16 plates. In addition to those numerous microcolonies, each plate contained from one to eight significantly larger colonies. Twenty-one of a total of about ninety larger colonies were purified by restreaking on lactose minimal plates plus kanamycin. Several of the kanamycin resistant microcolonies were also purified to serve as controls.

Genetic techniques and physical mapping. Transduction of Tn5 insertions by P1vir was carried out as previously described (Miller, J. H., Experiments in Molecular Genetics, Cold Spring Harbor Laboratory Press, Cold Spring Harbor, New York (1972), except recipient strains were diluted 1:20 from a fresh overnight culture and grown at 37° C. for two hours prior to adding the transducing lysate. HFr mapping was carried out as previously described (Wanner, B. L., *J. Mol. Biol.* 191:39-58 (1986)) using a set of Hfr::Tn10 strains (Table 1). The physical map location of the LC24 Tn5 insertion was obtained by Southern blot analysis (Chomczynski, P. et al., *Biochem. Biophys. Res. Commun.* 122:340-344 (1984)). MC1061 digested with BamHI, HindIII, EcoRI, EcoRV, BglII, KpnI, PstI, or PvuII was probed with flanking DNA from the LC24 insertion, and the resulting restriction patterns were compared with the physical map of the *E. coli* genome generated by Kohara, Y. et al., *Cell* 50:495-508 (1987) in the region around nirR.

TABLE 1

| Bacterial strains and plasmids | | |
|---|---|---|
| | Relevant characteristics | Source or reference |
| Strain | | |
| *E. coli:* | | |
| MC1061 | araD139 Δ(ara leu)7697 1271acX74 galU galK hsr hsm strA | Casadaban & Cohen '80 |
| Mph82 | lon::Tn10 (SW7J2B) | Boyd, 1987 |
| HA62 | MC1061 with lon::Tn10 from Mph82 | This work |
| HA63 | LC23 with lon::Tn10 from Mph82 | This work |
| HA64 | LC24 with lon::Tn10 from Mph82 | This work |
| LC12 | Tn5 mutant of MC1061 (snoA) | This work |
| LC4 | Tn5 mutant of MC1061 (snoB) | This work |
| LC6 | Tn5 mutant of MC1061 (snoB) | This work |
| LC23 | Tn5 mutant of MC1061 (snoB) | This work |
| LC25 | Tn5 mutant of MC1061 (snoB) | This work |
| LC24 | Tn5 mutant of MC1061 (snoC) | This work |
| C-1A | prototroph | Sasaki et al., 1965 |
| LC241A | C-1A containing LC24 Tn5 | This work |
| BW6160 | Hfr::Tn10 | Wanner, 1986 |
| BW7620 | Hfr::Tn10 | Wanner, 1986 |
| BW5660 | Hfr::Tn10 | Wanner, 1986 |
| BW6175 | Hfr::Tn10 | Wanner, 1986 |
| BW6164 | Hfr::Tn10 | Wanner, 1986 |
| NK6051 | Hfr::Tn10 | Wanner, 1986 |
| BW6165 | Hfr::Tn10 | Wanner, 1986 |
| BW6156 | Hfr::Tn10 | Wanner, 1986 |
| BW7261 | Hfr::Tn10 | Wanner, 1986 |
| BW7623 | Hfr::Tn10 | Wanner, 1986 |
| BW7622 | Hfr::Tn10 | Wanner, 1986 |
| BW5659 | Hfr::Tn10 | Wanner, 1986 |
| BW6163 | Hfr::Tn10 | Wanner, 1986 |
| BW6169 | Hfr::Tn10 | Wanner, 1986 |
| BW6166 | Hfr::Tn10 | Wanner, 1986 |

TABLE 1-continued

| | Bacterial strains and plasmids | |
|---|---|---|
| | Relevant characteristics | Source or reference |
| CAG12169 | zch-506::Tn10 | Singer et al., 1989 |
| CAG12028 | zci-233::Tn10 | Singer et al., 1989 |
| CAG12081 | zcj-3061::Tn10 | Singer et al., 1989 |
| CAG12026 | trg-2::Tn10 | Singer et al., 1989 |
| Plasmids: | | |
| pSDC13 | M13 ori, ColE1 ori, Cm-r | Levinson et al., '84 |
| pEH32 | pSDC13 with lacZ-nifA (NifA-AUG1) | Huala & Ausubel '89 |
| pEHΔR1 | pSDC13 with lacZ-nifA (NifA-ΔN) | Huala & Ausubel '89 |
| pMB210 | nifH-lacZ, RK2 ori, Tc-r | Better et al., 1985 |
| pLAC | lacZ, RK2 ori, Tc-r | Huala & Ausubel '89 |

References:
Better et al., EMBO J. 4:2419–2424 (1985)
Boyd, D. et al., in Phosphate Metabolism and Cellular Regulation in Microorganisms, A. Torriani-Gorini et al., eds., Am. Soc. Microbiol., Washington, pp. 89–93 (1987)
Casadaban et al., J. Mol. Biol. 138:179–297 (1980)
Haula, E. et al., J. Bacteriol. 171:3354–3365 (1989)
Levinson et al., J. Mol. Appl. Genet. 2:507–517 (1984)
Sasaki et al., Can. J. Gen. Micro. 40:365–376 (1965)
Singer et al., Microbiol. Rev. 53:1–24 (1989)
Wanner, B. L., J. Mol. Biol. 191:39–58 (1986)

$\beta$-galactosidase assays. Bacterial strains containing a lacZ-NifA expressing plasmid (pEH32 or pEHΔR1) and a nifH-lacZ reporter plasmid (pMB210) were grown in LB medium plus antibiotics at 28° C. under a continuous stream of 1% oxygen or 21% oxygen as previously described (Huala, E. et al., J. Bacteriol, 171:3354–3365 (1989)). The amount of active NifA present after 16 hours of growth was measured by assaying the cultures for $\beta$-galactosidase activity (Miller, J. H., Experiments in Molecular Genetics, Cold Spring Harbor Laboratory Press, Cold Spring Harbor, New York (1972)).

Immunological techniques. Antibodies were prepared against a peptide containing the last 14 amino acids of R. meliloti NifA (NH$_3$-Gly-Tyr-Ala-Leu-Arg-Arg-His-Gly-Val-Asp-Val-Arg-Lys-Leu-COOH) which was synbthesized by techniques known in the art (Bodanszky, M, Peptide Chemistry: A Practical Textbook, Springer-Verlag, New York, (1988). The peptide was conjugated using m-maleimidobenzoyl-N-hydroxysuccinimide ester (MBS; Pierce) to a carrier protein, keyhole limpet hemocyanin (Sigma), through an extra cysteine residue added at the amino terminus of the peptide. The carrier protein (10 mg) was dissolved in 0.7 ml 1 M potassium phosphate buffer, pH 7.3, and diluted to 7 ml in deionized water. MBS (6 mg) was dissolved in 100 µl of 50% dimethyl formamide, 50% tetrahydrofuran, and added dropwise to the carrier protein with constant stirring. Following the addition of 6 mg peptide, the reaction was stirred at room temperature overnight, then dialyzed 24 hr against 4 liters of phosphate buffered saline. Immunization of two New Zealand Red rabbits was carried out subcutaneously with 0.67 ml conjugated peptide emulsified with 0.33 ml Freund's complete adjuvant (Calbiochem) followed by two boosts, with 0.5 ml conjugated peptide and 0.5 ml Freund's incomplete adjuvant, at 16 and 31 days after the initial injections.

Western blots were performed as previously described (Blake, M. S. et al., Anal. Biochem. 136:175–179 (1984)) with alkaline phosphatase-conjugated goat anti-rabbit IgG (Cal-biochem) as the secondary antibody. Nitro blue tetrazolium and 5-bromo-4-chloro-3-indolyl phosphate for the alkaline phosphatase reaction were from Sigma.

Pulse-chase and Immunoprecipitation. Cultures containing pEHΔR1 were grown overnight in LB medium, then diluted 1:100 in M9 medium plus 0.5% glycerol, 40µg/ml L-amino acids except methionine and cysteine, 0.5 mg/l thiamine, and antibiotics, and grown aerobically in an environmental shaker at 37° C. for several hours. When the optical density of the culture at 600 nm reached a level between 0.1 and 0.5, the cultures were diluted to an optical density of 0.1 in the same medium, and grown at 28° C. for two hours in an environmental shaker. The cultures were pulse-labelled by addition of 37.5 µCi/ml of L-[$^{35}$S]methionine (1245 Ci/mmol) followed after two minutes by addition of excess unlabelled L-methionine to a final concentration of 1.4 mg/ml (Parsell, D. A. et al., J. Biol. Chem. 264:7590–7595 (1989)), and maintained at 28° C. throughout the chase period. At intervals 0.5 ml aliquots were added at 35 µl of 60 mM phenylmethylsulfonyl fluoride (PMSF) and 80 mM sodium azide in 90% ethanol on ice. Labelled cells were collected by centrifugation, resuspended in 30 µl SDS sample buffer (125 mM Tris [pH 6.8], 5 mM EDTA, 10% glycerol, 5% $\beta$-mercaptoethanol, 2% sodium dodecyl sulfate) and boiled for 5 minutes.

Immunoprecipitation of pulse-labelled samples was carried out by adding 10 to 30 µl of the boiling lysate to 970 µl phosphate-buffered saline and 5 µl of antiserum, agitating overnight at 22° C., and precipitating the bound antibodies using protein A-Sepharose (Pharmacia) as previously described (Storz, G. et al., J. Bacteriol. 171:2049–2055 (1989)). NifA protein was released from the washed protein A-Sepharose pellet by boiling in SDS sample buffer (as above) for 5 minutes, and the samples were electrophoresed on a 10% polyacrylamide SDS gel.

Tn5 cloning and sequence analysis. Chromosomal DNA from mutants LC12, LC23 and LC24 was digested with EcoRI, SalI or BamHI and ligated into pMLC28. The resulting kanamycin resistant colonies contained plasmids carrying part or all of the Tn5 insertion and flanking DNA. The DNA adjacent to the Tn5 insertions was sequenced by the dideoxy methoxy (Sanger, F. et al., Proc. Natl. Acad. Sci. USA 74:5463–5567 (1977)) using a Sequenase kit (U.S. Biochemical) with a Tn5-specific primer (3'-GTTCATC-GCAGGACTTG-5'; Ronson, C. W. et al., J. Bacteriol. 169:2424–2431 (1987b)). The primer may be made by techniques known in the art (Gait, M. J., et., Oligonucleotide Synthesis, A Practical Approach, IRS Press, Washington, DC, (1984)).

Growth curves. It has been previously reported that mutants in dcp are incapable of cleaving N-acetyl-ala-ala-ala and therefore cannot grow on this compound as the sole nitrogen source (Deutch, C. E. et al., *Proc. Natl. Acad. Sci. USA* 75:5998–6001 (1978)). To test whether the LC24 Tn5 insertion is located in dcp, the Tn5 insertion from LC24 was transduced to a prototrophic *E. coli* strain, C-1A. The resulting strain, LC241A, was grown overnight at 37° C. in M63 minimal medium, diluted 1:10 in M63, grown for several hours until the optical density (OD) exceeded 0.05 at 600 nm. Each culture was diluted to an OD of 0.05 in M63, then diluted 1:100 in either M63 (10 mg/ml ammonium sulfate) or in M63 without ammonium sulfate containing 10 mM N-acetyl-ala-ala-ala (Sigma) as the sole nitrogen source, and the growth of the cultures was observed by measuring optical density of the cultures at 600 nm periodically for 24 hours.

EXAMPLE 1

Tn5 mutagenesis and selection of mutants

*E. coli* strain MC1061, carrying the lacZ-NifA expression plasmid pEH32 and the nifH-lacZ reporter plasmid pMB210, was mutagenized with Tn5 and plated on lactose minimal plates, where wild type MC1061 grew very poorly, producing barely visible colonies after 84 hours of growth at 28° C. Mutants with an increased level of NifA activity, resulting in an increased ability to activate expression of the nifH-lacZ fusion, were expected to appear as larger colonies against a background of microcolonies. Twenty-one large kanamycin resistant colonies were isolated by restreaking on lactose minimal medium and their large size verified by plating each one on lactose minimal medium and comparing them to wild type MC1061 carrying pEH32 and pMB210. The absence of a Tn5 insertion on the plasmids carried by the mutants was verified by isolating plasmid DNA from each mutant and transforming *E. coli* MC1061. No kanamycin resistant colonies resulted, indicating that the Tn5 insertions were located on the chromosome.

Figure 1B:
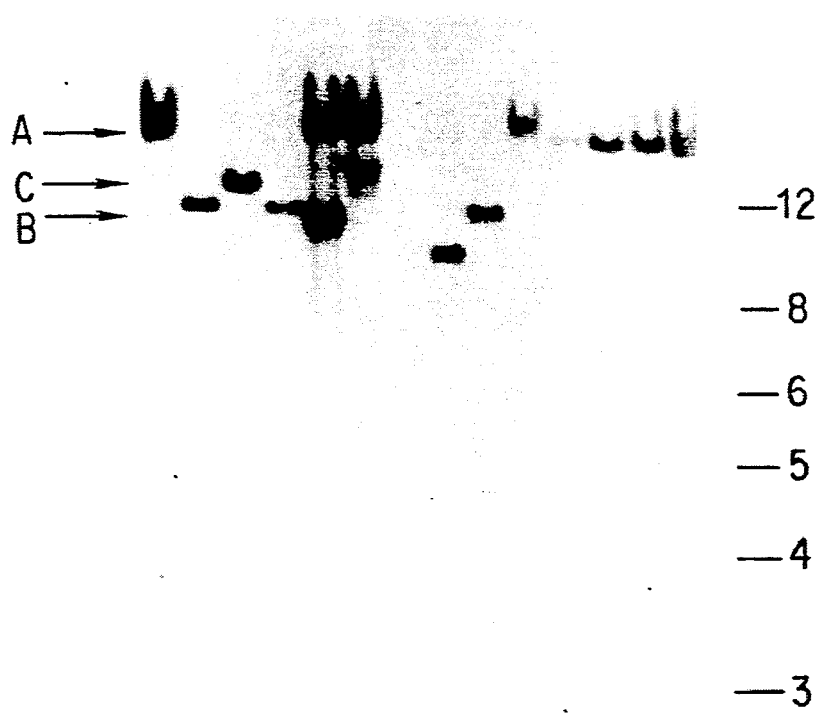
Figure 2:
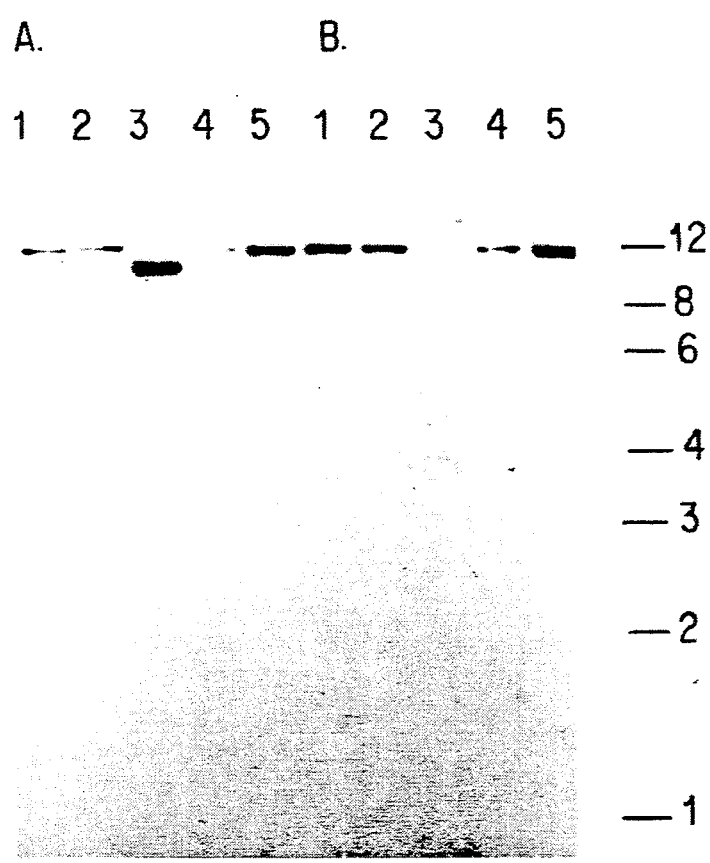
FIG. 2. Southern block of EcoRI (A) and EcoRV (B) restricted DNA from strains LC4, LC6, LC17, LC23, and LC25, probed with Tn5. Lane 1, LC4 (snoB); lane 2, LC6 (snoB); lane 3. LC17 (snoA); lane 4, LC23 (snoB); lane 5, LC25 (snoB). Strain LC17, which originally appeared to have an insertion at snoB (FIG. 1), was reclassified as a snoA insertion as a result of this experiment. Molecular weights are shown in kilobases on the right.
Figure 3:
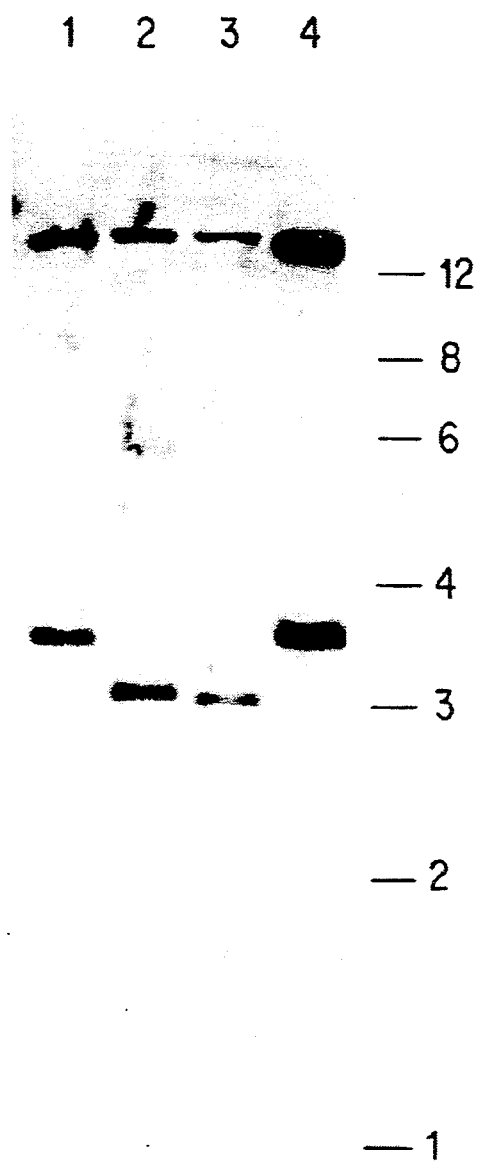
FIG. 3. Position of snoB insertions relative to SalI site in alaS. Southern block of SalI restricted DNA from strains LC4 (1), LC6 (2), LC23 (3), and LC25 (4) probed with Tn5. Molecular weights are shown in kilobases on the right.

Chromosomal DNA from each mutant strain was prepared, digested with EcoRI and analyzed on a Southern blot using a Tn5 probe (FIG. 1). Four mutants carrying more than one Tn5 insertion (LC9, LC11, LC21, LC22) and two other insertions with weak phenotypes (LC5, LC18) were not characterized further. The remaining Tn5 insertions were found to occur in three different EcoR1 fragments. Group 1 (snoA, for stability of NifA in oxygen) consisted of 10 members (LC2, LC3, LC7, LC8, LC10, LC12, LC13, LC14, LC15, LC16; FIG. 1). Group 2 (snoB) consisted of 4 members (LC4, LC6, LC23, LC25; FIG. 2) and Group 3 (snoC) consisted of one member (LC24; FIG. 2). One representative from each group (LC12, LC23, and LC24) was chosen for further characterization. The approximate genetic locations of snoA, snoB and snoC were determined by Hfr mapping to be between 6 and 13 min for snoA, between 23 and 30 min for snoB, and between 50 and 61 min for snoC.

EXAMPLE 2

Characterization of the Mutant Phenotypes

Mutants LC12, LC23 and LC24 containing the plasmids pEH32 (NifA-AUG1) and pMB210 (nifH-lacZ) were grown in LB medium under a continuous stream of either 1% and 21% oxygen for 16 hours and assayed for β-galactosidase activity from the nifH-lcZ reporter fusion. When grown at 21% oxygen, all three mutants showed levels of β-galactosidase activity about ten fold higher than wild type MC1061 containing pEH32 and pMB210. At 1% oxygen, LC12 and LC24 showed slightly elevated levels of β-galactosidase activity relative to MC1061, while LC23 showed no relative increase in β-galactosidase activity. To confirm that the phenotypes of the mutants were caused by the Tn5 insertions rather than an unlinked point mutations, the Tn5 insertions of strains LC12, LC23 and LC24 were transduced into MC1061 using phage P1. The transductants were transformed with pEH32 and pMB210 and assayed for β-galactosidase activity at 21% oxygen. The transducer strains, like the original mutants, showed a ten fold elevated level of β-galactosidase activity relative to MC1061 (Table 2). The increased level of β-galactosidase activity in the mutant strains was fully dependent on the presence of NifA. No increase in the basal level of activity due to constitutive activity of the nifH promoter was seen in the absence of NifA in any of the mutants (Table 2).

TABLE 2

NifA activity in wild type and mutant *E. coli.*

| Strain | β-galactosidase Activity | |
|---|---|---|
| | 1% oxygen | 21% oxygen |
| MC1061 | 7.6 | 7.9 |
| MC1061 + pMB210 | 144 | 169 |
| LC12 + pMB210 | 99 | 164 |
| LC23 + pMB210 | 135 | 129 |
| LC24 + pMB210 | 133 | 183 |
| MC1061 + pMB210, pEH32 | 46,128 | 1,367 |
| LC12 + pMB210, pEH32 | 67,902 | 12,650 |
| LC23 + pMB210, pEH32 | 48,789 | 13,859 |
| LC24 + pMB210, pEH32 | 60,341 | 15,163 |
| MC1061 + pMB210, pEHΔR1 | 53,189 | 35,836 |
| LC12 + pMB210, pEHΔR1 | 60,017 | 42,847 |
| LC23 + pMB210, pEHΔR1 | 54,584 | 28,660 |
| LC24 + pMB210, pEHΔR1 | 57,398 | 45,205 |
| MC1061 + pLAC | 41,420 | 32,901 |
| LC12 + pLAC | 37,615 | 30,452 |
| LC23 + pLAC | 31,538 | 25,882 |
| LC24 + pLAC | 34,133 | 29,388 |

β-galactosidase activity is given in Miller units. pEH32 expresses NifA-AUG1 from the lacZ promoter. pEHΔR1 expresses NifA-ΔN from the lacZ promoter. pMB210 carries a nifH-lacZ reporter fusion. pLAC expresses the lacZ gene from its natural promoter.

The effect of the sno mutations on a more stable mutant form of NifA carried on plasmid pEHΔR1 was also tested. Strains LC12, LC23 and LC24 containing pEHΔHI and pMB210 were tested for β-galactosidase activity at 1% and 21% oxygen (Table 2). Only a small increase in NifA-ΔN activity was observed in LC12 (snoA) and LC24 (snoC), *while no increase in activity was observed in* LC23 (snoB).

EXAMPLE 3

Demonstration that the snoA mutations are in lon

Hfr mapping of the snoA insertion in LC12 showed that the location of snoA was between 6 and 13 minutes on the *E. coli* genetic map. The location of the insertion on the physical map (Kohara et al., *Cell* 50:495–508 (1987)) was determined by Southern analysis to be about 55 kb from proC (the nearest genetic marker on the map of Kohara et al., *Cell* 50:495–508 (1987)) in the vicinity of lon. The Tn5 insertion and flanking DNA from LC12 was cloned and about 300 base pairs on either side of the Tn5 insertion were sequenced. Sequence 1, below, represents the reconstructed sequence (the Tn5 sequence and duplication of the insertion site having been removed) which was present in the host prior to Tn5 insertion. Tn5 insertion had occured following nucleotide 305.

the Tn5 insertions in LC4, LC6, and LC25 were also near we measured the frequency of cotransduction of these Tn5 insertions with a srlC300::TN10 insertion from strain BW5660 (Wanner, B. L., *J. Mol. Biol.* 191:39-58 (1986)) We found that all four snoB Tn5 inser-

```
                          Sequence 1
  1 CTTTTCTGCG  AAGGXGGAGT  ATCTGGAGTC  GCCGACCATT  GATGAGCGGG

51 AACAGGAAGT  GCTGGTGCGT  ACTGCAATCA  GCCAGTTCGA  AGGCTACATC

101 AAGCTGAACA  AAAAAATCCC  ACCAGAAGTG  CTGACGTCGC  TGAATAGCAT

151 CGACGATCCG  GCGCGTCTGG  CGGATACCAT  TGCTGCACAT  ATGCCGCTGA

201 AACTGGCTGA  CAAACAGTCT  GTTCTGTTCT  GGAGATCTCC  GACGTTAACG

251 AACGTCTGGA  ATATCTGATG  GCAATGATGG  AATCGGAAAT  CGATCTGCTG

301 CAGGTTGAGA  AACGCATTCG  CAACCGCGTT  AAAAAGCAGA  TGGAGAAATC

351 CCAGCXTGAG  TACTATCTGT  CTGAACGAGC  AAATGAAAGC  TATTCAGAAA

401 GAACTCGGTG  AAATGGACGA  CGCGCCGGAC  GAAAXGAAGC  CCTGAAGCGC

451 AAAATCGACG  CGGCGAAGAT  GCCGAAAGAG  GCAAAAGAGA  AAGCGGAAXX

501 AGAGTTGCAG  AAGCTGAAAA  TGATGTCTCC  GATGTCGGCA  GAAGCGACCG

551 TAGTGCGTGG  TTATATCGAC  TGGATGGTAC  AGGTXCCGTG  GAATGCGCGT

601 CAAGAGGTCA  AAAAAGXCCT  GCGTCXGGCG  CAGGAAATCC  TTGATACCGA

651 CCATTATGGT  CTGGAGCGCG  TGAAAGATCG  AATCCTTGAG  TATCTTGCGG

701 TTCAAAGCCG  TGTCAACAAA  ATCAAGGGAC  CGATCCTCTG  CCTGGTAGGG

751 CCGCCGGGGG  TAGGTAAAAC  CTCTCTTGGT  CAGTCCATTG  CCAAAGCCAC

801 CGGGCGTAAA  TATGTCCGTA  TGGCGCTGGG  CGGGCGTGAT  GAAGCGGAAA

851 TCCGTGGTCA
```

This sequence allowed us to determine that the LC12 insertion is within the lon gene, which encodes the protease La. The Tn5 insertion in LC12 follows nucleotide 1038 of the lon sequence reported by Chin et al., *J. Biol. Chem.* 263:11718-11728 (1988), and has resulted in the duplication of a PstI site located about one fourth of the way through the lon coding region.

EXAMPLE 4

Location of snoB

The Tn5 insertion from LC23 (snoB) was cloned and a 236 base pair region of flanking DNA was sequenced. The sequence of one end of the host genetic sequences at the Tn5 insertion site in LC23 is presented in sequence 2, below.

tions were cotransduced at a high frequency with srlC (Table 3). Southern analysis using SalI restricted DNA from LC4, LC6, LC23 and LC25 showed that two insertions (LC23 and LC6) are located about 400 base pairs downstream from a SalI site near the 3' end of alaS, and the other two insertions (LC4 and LC25) are about 750 base pairs from this SalI site.

TABLE 3

| | snoB cotransduction with srlC::tn10 | | |
|---|---|---|---|
| Strain* | Colonies Tested | Colonies Tc$^R$ | % Cotransduction |
| LC4 (snoB) | 8 | 0 | 100 |
| LC6 (snoB) | 9 | 0 | 100 |
| LC23 (snoB) | 7 | 1 | 86 |
| LC25 (snoB) | 10 | 1 | 90 |
| LC24 (snoC) | 6 | 6 | 0 |

```
                          Sequence 2
  1 TAGCGATATA  CACAACTTCA  ACCTGACTTT  ATCGTTGTCG  ATAGCGTTAA

51 TGCGAATGCC  GTGAAGCGAG  TCCACGGCAT  TGCCTGACGC  TTATATTATT

101 GCAATTTCGC  GCTGACCCAG  CCTTTCACAC  TGGCTAACGC  TGCAGGTAAG

151 GCCGCAGCAT  CCGTACCACC  GGCTTGCGCC  ATGTCAGGAG  CTCCACCACC

201 CTTGCCGCCC  ACCTGCTGAG  CGACCATACC  AATCAG
```

A search of the Genbank sequence database using the sequence of the flanking DNA revealed that the Tn5 insertion in this mutant is located approximately 160 base pairs downstream of the termination codon for alaS, encoding alanyl tRNA synthetase (Putney, S. D. et al., *Science* 213:1497-1501 (1981)). To confirm that

*Donor strains in P1 transduction. Kanamycin resistant BW5660 recipient colonies carrying a transduced Tn5 insertion were scored for tetracycline resistance, indicating the presence of the srlC::Tn10 insertion.

EXAMPLE 5

Location of snoC

The 221 base pairs of flanking DNA from the LC24 (snoC) insertion were cloned and sequenced. The sequence of one end of the host genetic sequences at the Tn5 insertion site in LC24 is presented in sequence 3, below.

Sequence 3

```
  1 AAAAAAGGAA GTAAGACAAT ATGGAGCGCA ACGCCCATCG CTTGACGTTG
 51 CATTCACCTG CAAGAGAGAT ATTGCCCTGA ATGGGTAGAG AGTTTATTGA
101 CTTCGCTCAA ACTTTGCGGC GTTTTTGTAT ACAGACAGCC GGAAAAATTG
151 CTTTTGTTAC AACCATTTAC TACGATGCAA CCATAAAGCA ACACCACCAA
201 TAAGAACAAC TAACAGAATA C
```

Figure 4:
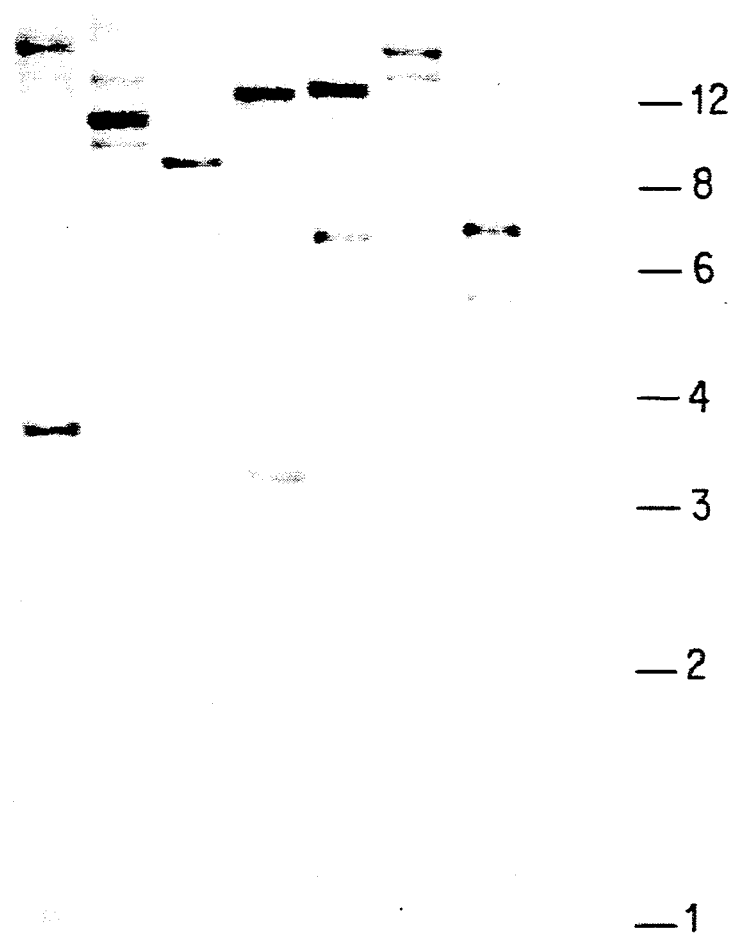
FIG. 4. Physical map position of Tn5 in LC24. Southern block of MC1061 DNA restricted with BamHI (1), HindIII (2), EcoRI (3), EcoRV (4), BglII (5), KpnI (6), PstI (7), and PvuII (8) probed with flanking DNA from the Tn5 insertion in LC24. The band with the most intense hybridization signal was chosen for each enzyme and the sizes of these fragments were used to determine the location of the Tn5 insertion in snoC on the physical map of Kohara, Y. et al., Cell 50:495–508 (1987). Molecular weights are shown in kilobases on the right.

The Genbank DNA sequence database was searched for a similar sequence, but no matching sequence was found. Since the rough location for this insertion had been determined by Hfr mapping to lie in the region of 23 to 31 minutes on the E. coli genetic map, P1 transduction was tested for with a series of Tn10 insertions in this region. A Tn10 insertion at 29.3 minutes (zcj-3061::Tn10) was determined to be 84% cotransducible with the LC24 Tn5 insertion (Table 4). The location of the insertion on the physical map of Kohara, Y. et al., Cell 50:495–508 (1987), was determined by Southern analysis of MC1061 DNA restricted with the eight mapping enzymes used in the generation of the physical map and probed with the cloned flanking DNA from the LC24 insertion (FIG. 4).

TABLE 4

| Recipient Strain | Location of snoC by P1 Transduction % Cotransduction | | |
|---|---|---|---|
| | Experiment 1 | Experiment 2 | Experiment 3 |
| CAG 12169 | 0%* (190)** | | |
| CAG 12028 | 7.1% (112) | 4% (482) | 11% (200) |
| CAG 12081 | 81% (170) | 84% (804) | |
| CAG 12026 | 0% (98) | 0.2% (579) | |

*% of kanamycin resistant colonies which were not tetracycline resistant.
**Total number of colonies scored.

The results of the physical and genetic mapping indicate that the LC24 insertion is located about 10 kilobases away from nirR (29.4 min) in the direction of rac. The dcp gene, which encodes dipeptidyl carboxypeptidase, maps in this vicinity (Deutch, C. E. et al., Proc. Natl. Acad. Aci. USA 75:5998–6001 (1978)). To determine whether the Tn5 insertion of LC24 falls within dcp, the Tn5 insertion of LC24 was transduced into the prototrophic strain C-1A to create strain LC241A and the effect of the insertion on the ability of this strain to grow in minimal medium using N-acetyl-ala-ala-ala as the sole nitrogen source was measured. While wild-type E. coli is capable of growing on this substrate, a dcp mutant is incapable of cleaving this tripeptide, and therefore cannot use it as a nitrogen source (Deutch, C. E. et al., Proc. Natl. Acad. Sci. USA 75:5998–6001 (1978)). Comparison of the growth rates of C-1A and LC241A revealed no difference in the ability of these strains to grow on N-acetyl-ala-ala-ala as the sole nitrogen source, indicating that the Tn5 insertion in LC24 may not be in dcp.

EXAMPLE 6

Accumulation of NifA Protein

To determine whether an increase in the accumulation of NifA-AUG1 was responsible for the increased level of $\beta$-galactosidase activity int he mutants, NifA-AUG1 accumulation in MC1061, HA62 (a lon::Tn10 derivative of MC1061), LC23 (snoB), and LC24 (snoC) was compared by Western blot. NifA-AUG1 accumulation at 1% oxygen was about equal in all four strains (FIG. 5A), but the accumulation at 21% oxygen varied. While NifA-AUG1 decreased to an undetectable level in MC1061 grown under 21% oxygen (FIG. 5B, lane 1), NifA-AUG1 in HA62 (lon) grown under the same conditions showed no decrease in accumulation (FIG. 5B, lane 2). Like HA62 (lon), LC24 (snoC) showed an increase in NifA-AUG1 accumulation at 21% oxygen (FIG. 5B, lane 4). However, no increase in NifA-AUG1 accumulation was seen in LC23 (snoB) grown under 21% oxygen (FIG. 5B, lane 3). These results suggest that the lon and snoC mutations in strains HA62 and LC24, respectively, may cause a decrease in the NifA degradation rate or an increase in the rate of NifA synthesis at high oxygen tension.1 By contrast, LC23 (snoB) did not appear to cause an increase in NifA-AUG1 accumulation under 21% oxygen, suggesting that the effect of a snoB mutation may be to increase the activity of NifA-AUG1 at 21% oxygen rather than its rate of accumulation, possibly through a decrease in the rate of NifA-AUG1 inactivation by oxygen.

Figure 6:
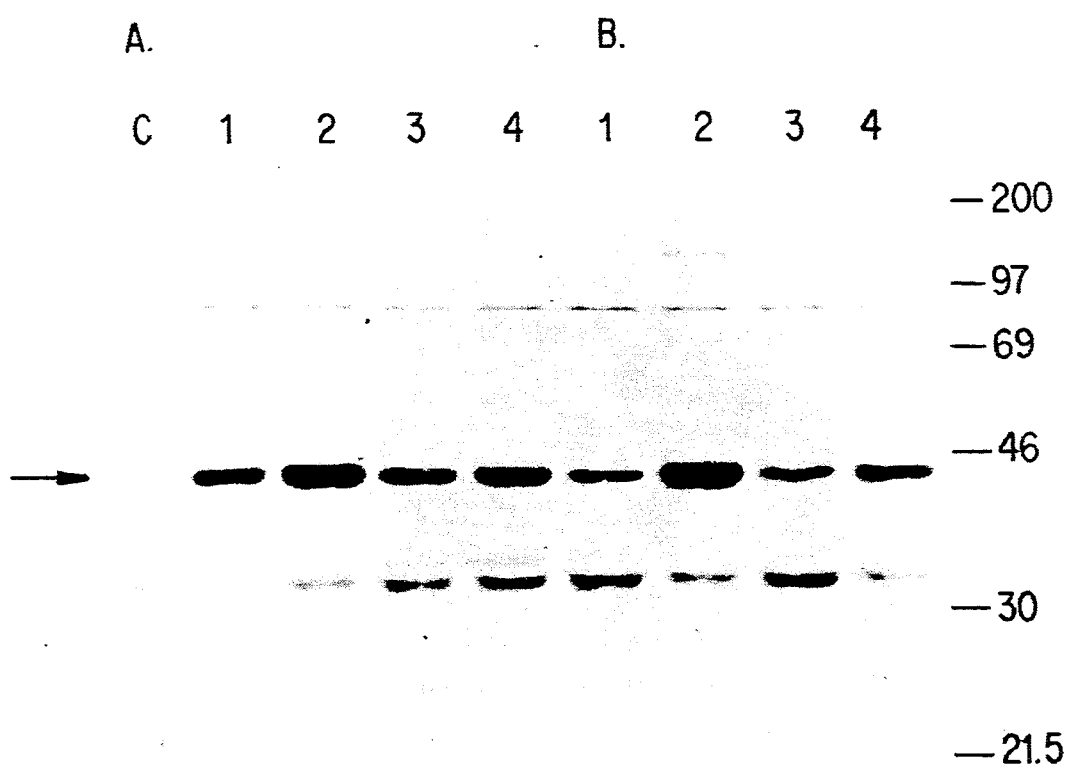
FIG. 6. Immunodetection of R. meliloti NifA-ΔN in MC1061 and mutant derivatives grown under 1% or 21% oxygen. (A) Cells grown under 1% oxygen. Lane C, MC1061 containing only vector (no NifA); lane 1, MC1061 with pEHΔRI (NifA-ΔN); lane 2, HA62 (lon) with pEHΔRI; lane 3, LC23 (snoB) with pEHΔRI; lane 4, LC24 (snoC) with pEHΔRI. (B) Cells grown under 21% oxygen, lanes as in part A. Positions of molecular weight markers are shown on the right (×0.001).

Although the sno mutations did not have any obvious effect on NifA-$\Delta$N activity, the accumulation of this mutant form of NifA in MC1061 and the three sno mutants (HA62, lon; LC23, snoB; and LC24, snoC) was also compared. In contrast to the results with NifA-AUG1, differences in accumulation under both 1% and 21% oxygen for NifA-$\Delta$N were found (FIG. 6). The accumulation of NifA-$\Delta$N in MC1061 is much higher under both 1% and 21% oxygen than accumulation of NifA-AUG1, probably due to an increase in protein stability, but accumulation is still lower at 21% oxygen (FIGS. 6A and 6B, lane 1; Huala, E. et al., J. Bacteriol. 171:3354–3365 (1989)). The lon mutation (HA62; FIG. 6A, lane 2) caused a visible increase in NifA-$\Delta$N accumulation even under 1% oxygen, and once again, prevented any decrease in accumulation at 21% oxygen (FIG. 6B, lane 2). The snoC mutation (LC24) also caused an increase in NifA-$\Delta$N accumulation under both 1% and 21% oxygen (FIGS. 6A and 6B, lane 4), while LC23 (snoB) showed no increased accumulation of NifA-$\Delta$N relative to MC1061 (FIGS. 6A and 6B, lane 3). Overall, the effect of the mutations on accumulation at 21% oxygen was similar for NifA-AUG1 and NifA-N.

Figure 7:
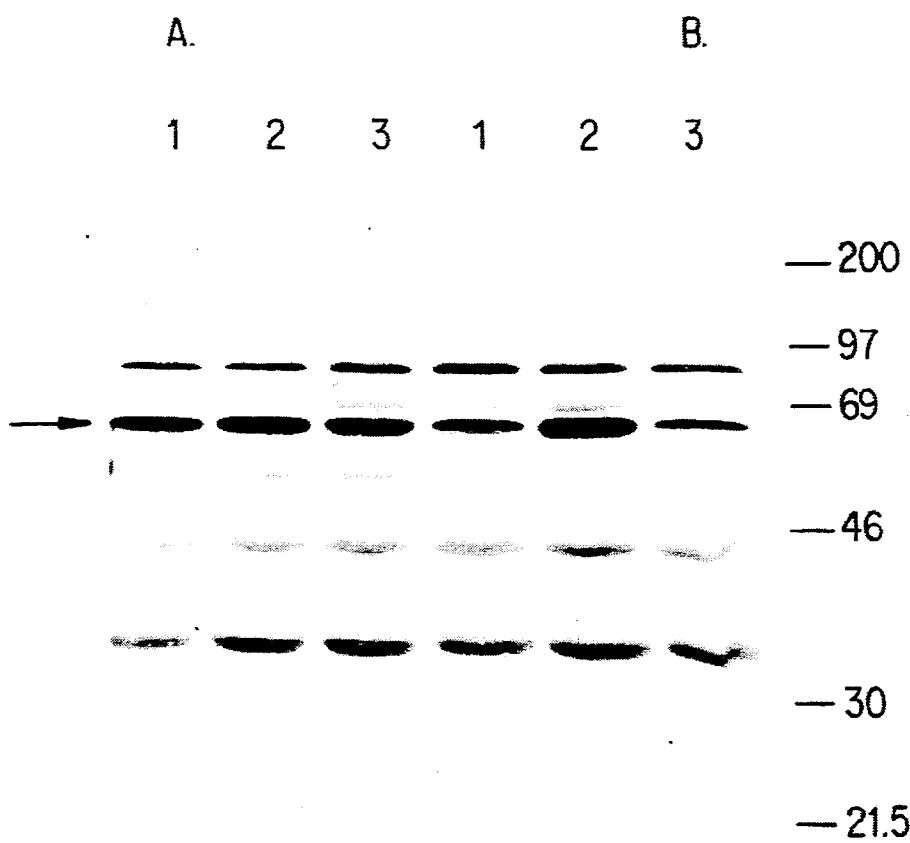
FIG. 7. Immunodetection of R. meliloti NifA-AUG1 in lon, snoB lon and snoC lon mutants grown under 1% or 21% oxygen. (A) Cells grown under 1% oxygen, Lane 1, HA62 (lon) with pEH32 (NifA-AUG1); lane 2, HA63 (snoB lon) with pEH32; line 3, HA64 (snoC lon) with pEH32. (B) Cells grown under 21% oxygen, lanes as in part A. Positions of molecular weight markers are shown on the right (×0.001).
Figure 8:
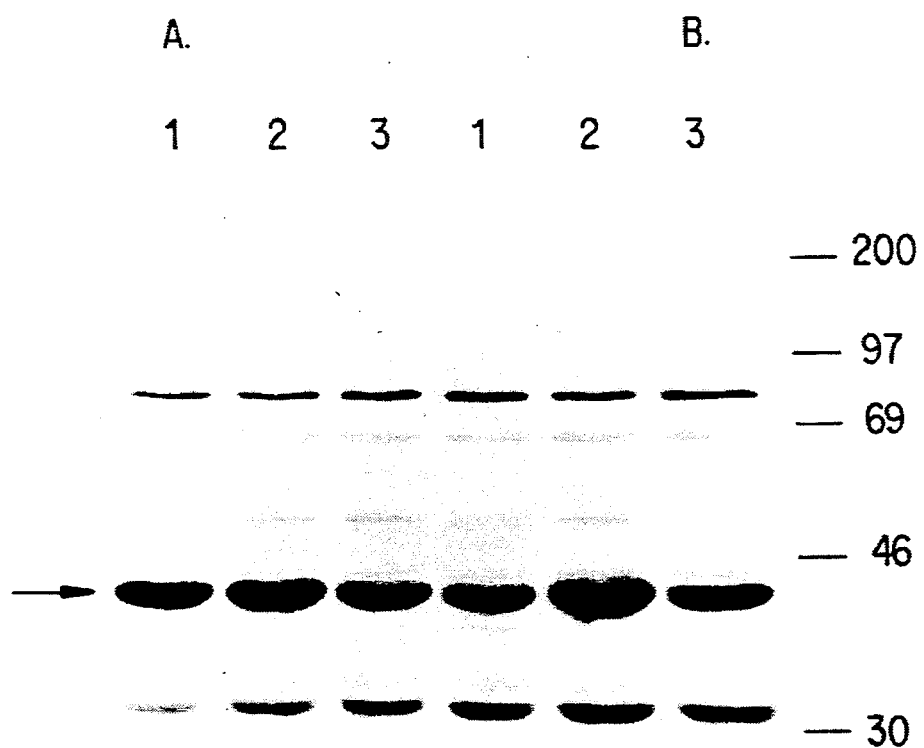
FIG. 8. Immunodetection of R. meliloti NifA-ΔN1 in lon, snoB lon and snoC lon mutants grown under 1% or 21% oxygen. (A) Cells grown under 1% oxygen. Lane 1, HA62 (lon) with pEHΔRI (NifA-ΔN); lane 2, HA63 (snoB lon) with pEHΔRI; lane 3, HA64 (snoC lon) with pEHΔRI. (B) Cells grown under 21% oxygen, lanes as in part A. Positions of molecular weight markers are shown on the right (×0.001).

The lon::Tn10 insertion of MpH82 was transduced into LC23 and LC24 to create strains HA63 (lon snoB) and HA64 (lon snoC). These double mutants were transformed with pEH32 or pEHΔR1 and the accumulation of NifA was observed on Western blots (FIGS. 7 and 8). HA64 (lon snoC; FIG. 7, lane 3) accumulated NifA-AUG1 to the same level as HA62 (lon; FIG. 7, lane 1), indicating that the effects of mutation in snoC and lon are not additive. However, HA63 (lon snoB; FIG. 7, lane 2) showed increased accumulation when compared to HA62 (lon). This result was unexpected since the snoB insertion appeared to have no effect on NifA-AUG1 accumulation by itself (FIG. 4).

The effect of lon snoB and lon snoC double mutations on accumulation of NifA-ΔN was also examined (FIG. 8). Once again, HA64 (lon snoC; FIG. 8, lane 3) accumulated NifA-ΔN to the same level as HA62 (lon, FIG. 8, lane 1), while HA63 (lon snoB; FIG. 8, lane 2) showed increased accumulation when compared to HA62 (lon). The effect of the lon snoC double mutant on accumulation of both NifA-AUG1 and NifA-ΔN suggests that the snoC gene product acts with the lon gene product to decrease the accumulation of NifA, since the NifA level is lowered only when a cell has wild type copes of both genes. In contrast, the snoB mutation somehow causes an increase in the susceptibility to degradation by the lon product without bringing about a net change in NifA accumulation.

EXAMPLE 7 sno Mutations Have No Effect on the lac Promoter

Figure 9:
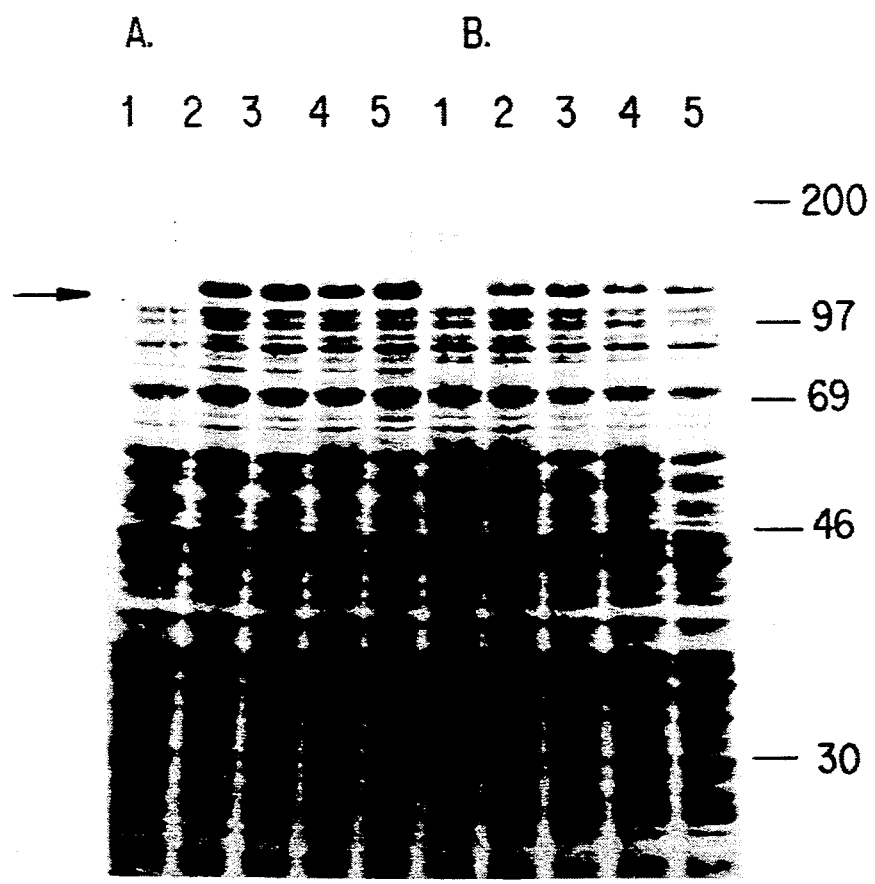
FIG. 9. Expression of β-galactosidase from the lacZ promoter. Sodium dodecyl sulfate (SDS) polyacrylamide gel of total protein. (A) Cells grown under 1% oxygen. (B) Cells grown under 21% oxygen. Lane 1, MC1061 with pMB210; lane 2, MC1061 with pLAC; lane 3, LC12 with pLAC; lane 4, LC23 with pLAC; lane 5, LC24 with pLAC. Arrow indicates position of β-galactosidase. Positions of molecular markers are shown on the right (×0.001).

Several explanations are possible for the observed increase in NifA accumulation in LC12 and LC24, including increased transcription of NifA from the lac promoter, an increase in the translation efficiency, or a decrease in the rate of NifA degradation. To test whether transcription from the lac promoter was increased in these mutants, the expression of β-galactosidase from a plasmid-borne copy of the lacZ gene expressed from its natural promoter (plasmid pLAC) was compared in E. coli MC1061, LC12 (snoA), LC23 (snoB) and LC24 (snoC) (Table 2). No difference in β-galactosidase activity was detected in the mutants, suggesting that the activity of the lac promoter and lac ribosome binding site was not affected by the mutations. The amount of β-galactosidase protein produced from pLAC in MC1061, LC12, LC24 and LC24 and also compared on a sodium dodecyl sulfate (SDS)-polyacrylamide gel. No differences in the level of β-galactosidase in MC1061 and the sno mutants were observed following growth at 1% or 21% oxygen (FIG. 9). Since the lacZ ribosome binding site and 5'-untranslated sequences are present in both the lacZ test plasmid and the lacZ-NifA fusion carried on pEH32, this result suggests that transcription and translation of NifA is not affected in LC12 and LC24, unless the presence of NifA rather than lacZ sequences downstream from the translational start site causes an increase in transcription or translation int he mutants.

EXAMPLE 8

Half-life of NifA protein

Figure 10A:
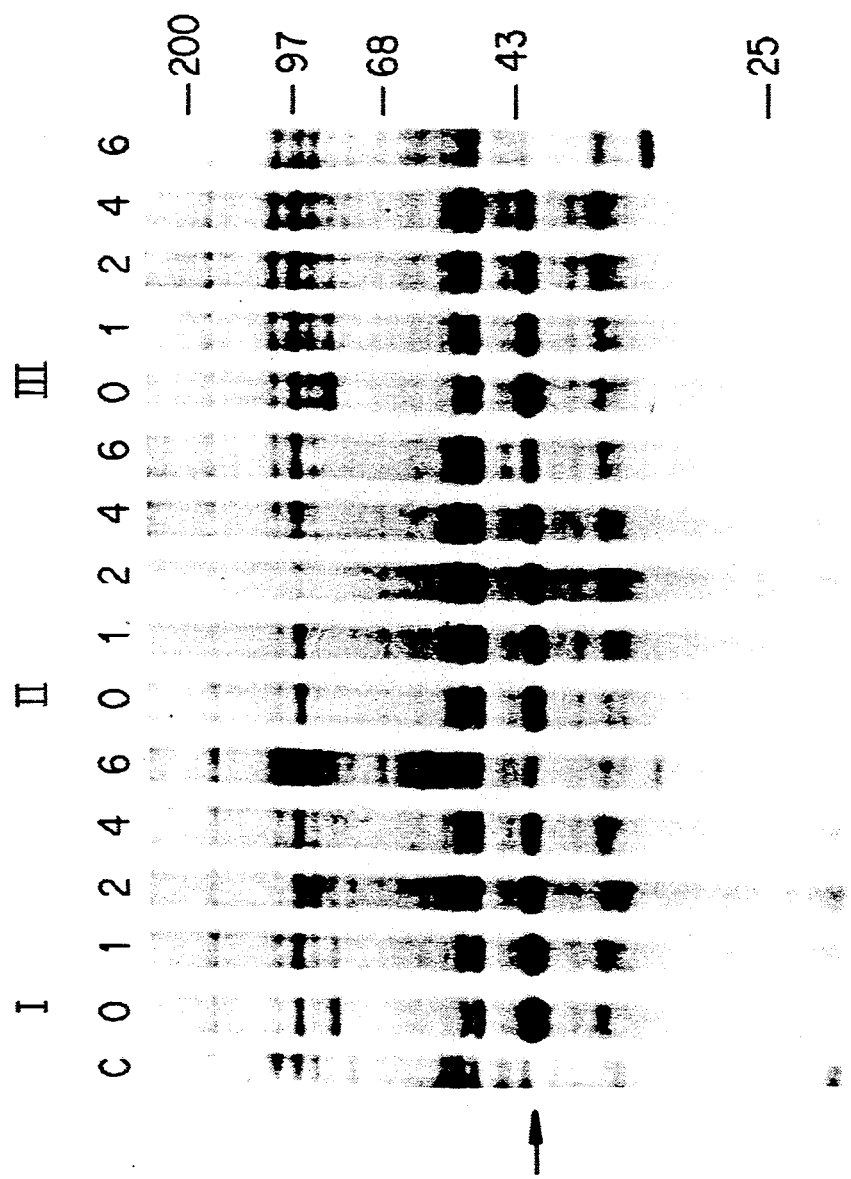
FIG. 10 (Parts A and B). Stability of NifA in MC1061 and mutant derivatives: sodium dodecyl sulfate polyacrylamide gel electrophoresis (SDS-PAGE) of immunoprecipitated NifA following a 2 minute pulse with [35S]-methionine and a chose of 0 to 6 hours with excess unlabeled methionine. The length of the chose for each lane is indicated in hours at the top of the figure. Lane C, MC1061 without pEHΔRI (no NifA-ΔN); (I), MC1061 with pEHΔRI; (II), HA62 (lon) with pEHΔRI; (no NifA-ΔN); (I), MC1061 with pEHΔRI; (II), HA62 (lon) with pEHΔRI; (III), LC23 (snoB) with pEHΔRI; (IV), LC24 with pEHΔRI; (V), HA63 lon snoB) with pEHΔRI; (VI); HA64 (lon snoC) with pEHΔRI. Positions of molecular weight markers are shown on the right (×0.001).
Figure 10B:
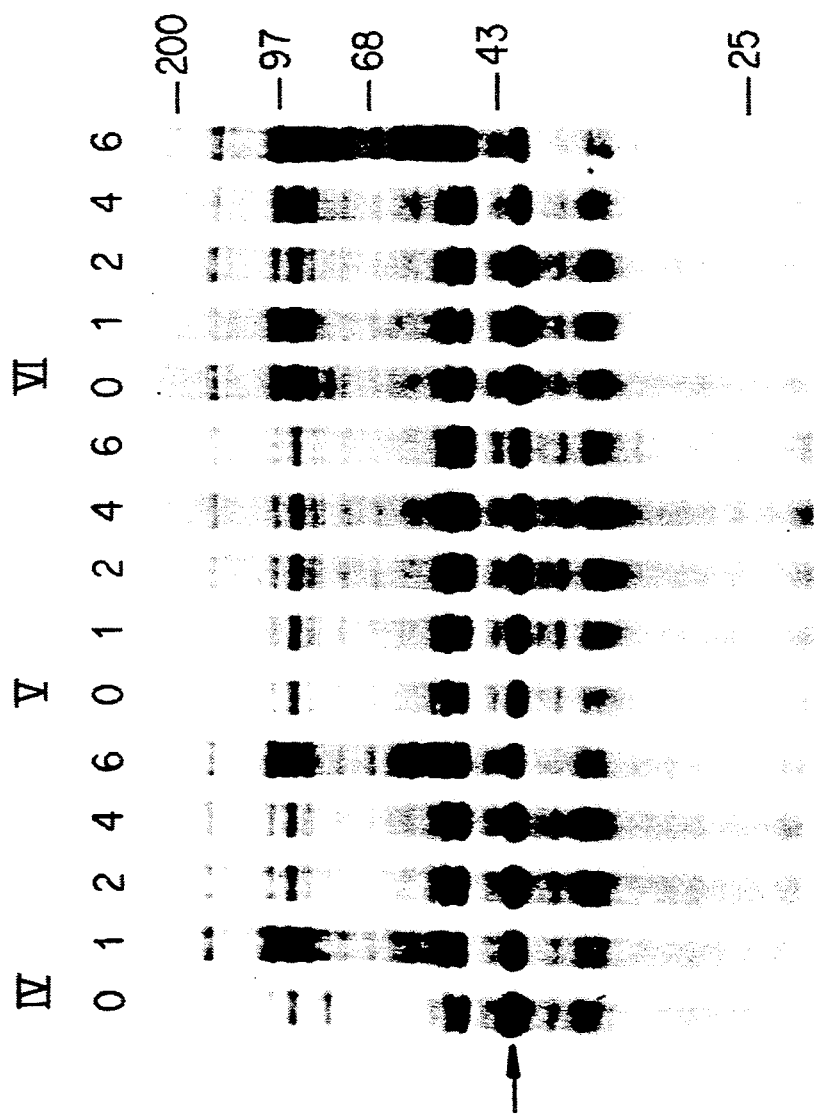
Figure 11B:
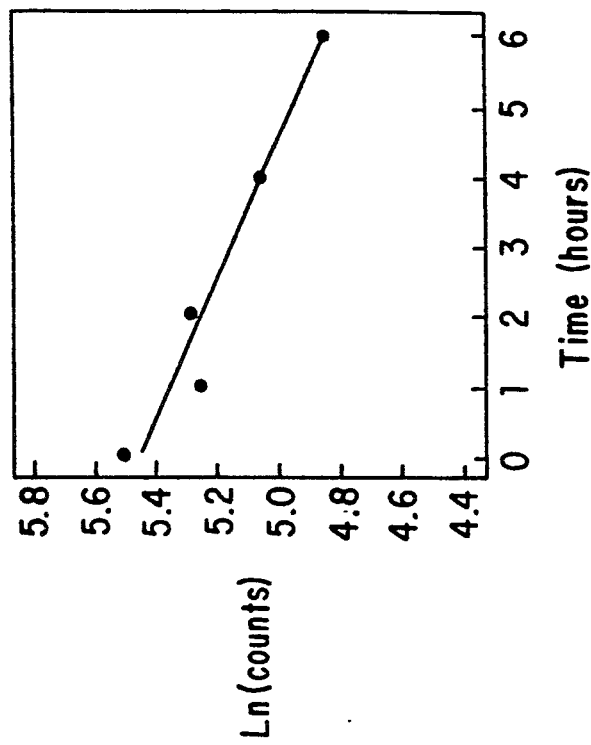
FIG. 11 (parts A-F). Half-life of NifA-ΔN in wild type and mutant strains. Amount of NifA is given as the natural log of the number of decay events detected over 1000 minutes for each NifA band visible in FIG. 10. (A), MC1061; (B), HA62 (lon); (C) LC23 (snoB); (D), HA63 (lon snoB); (E), LC24 (snoC); (F), HA64 (lon snoC).
Figure 11A:
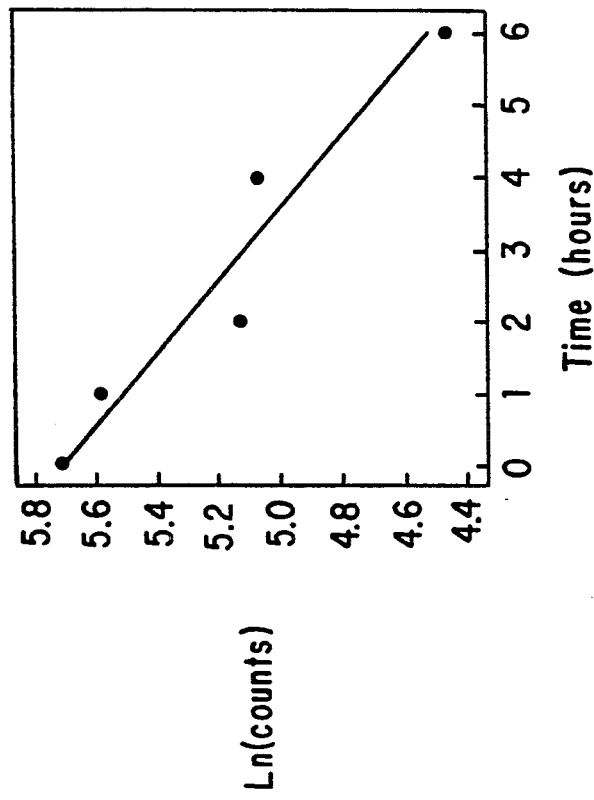
Figure 11D:
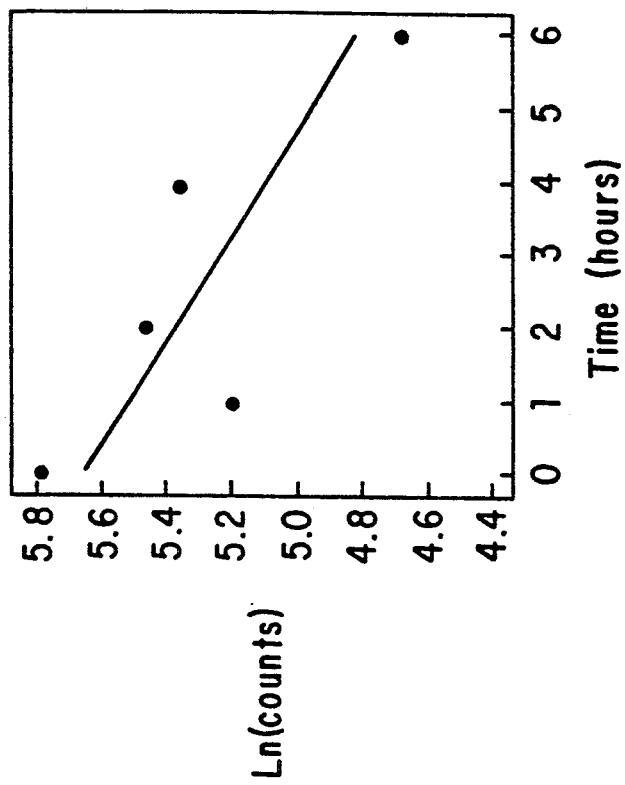
Figure 11C:
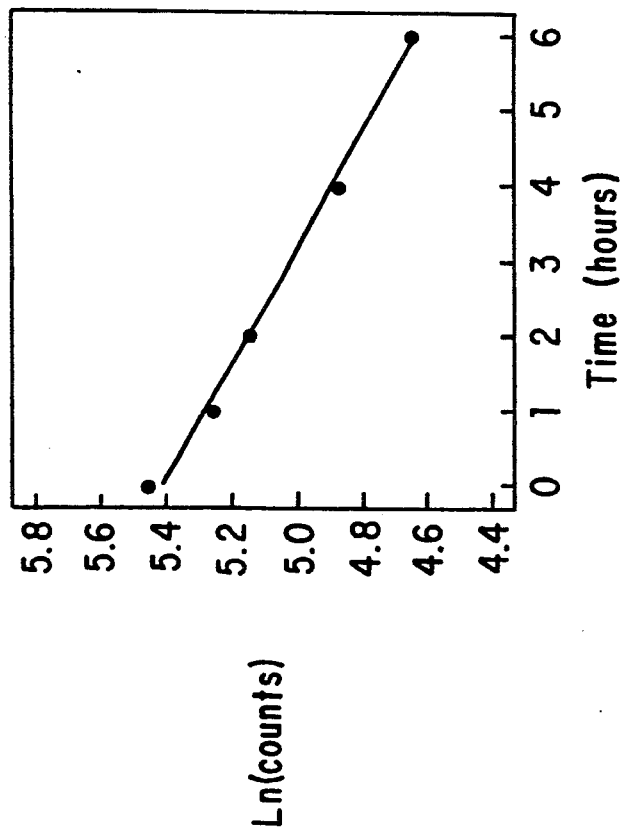
Figure 11F:
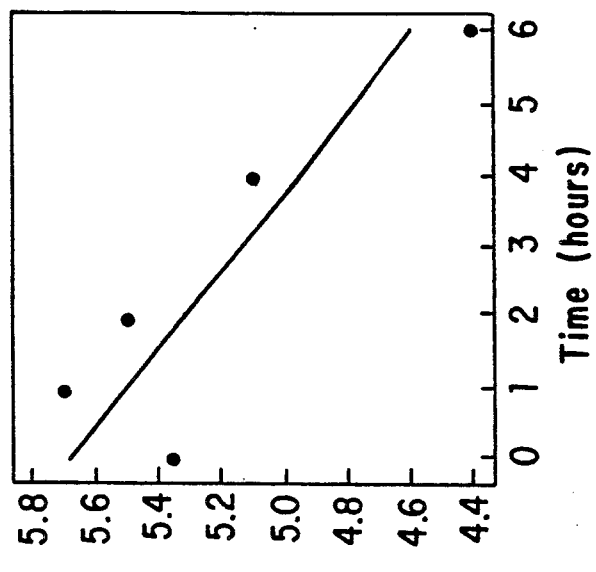
Figure 11E:
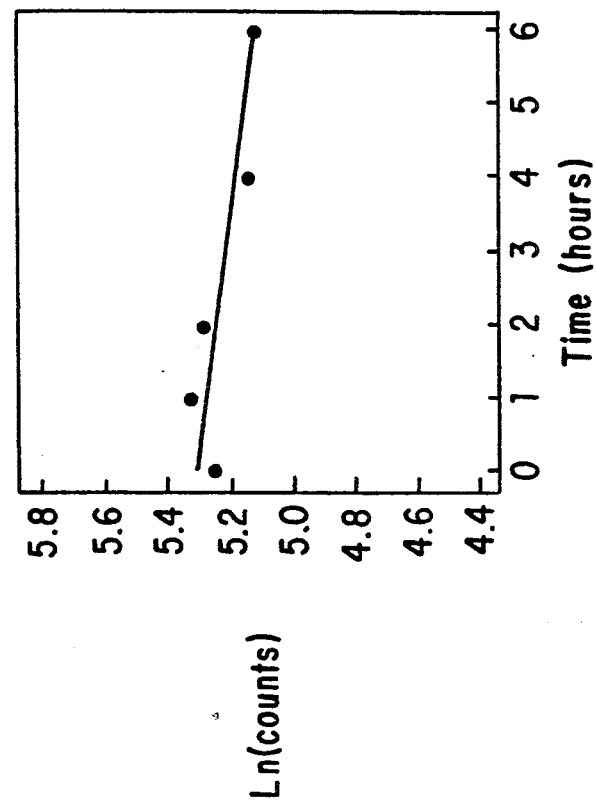

To compare the rates of NifA synthesis and degradation in MC1061 and the sno mutants, aerated log-phase cells were pulse-labeled for two minutes and the decline of labelled NifA was monitored. As the half-life of NifA-AUG1 appeared to be shorted than two minutes, making reliable measurement difficult, we the half-life of the more stable NifA-ΔN was measured (FIGS. 10 and 11; Table 5). Although the activity of NifA-ΔN was increased only slightly by the lon, snoB or snoC mutations, these mutations did affect the accumulation of NifA-ΔN and NifA-AUG1 at 21% oxygen in a similar way. The half-life of NifA-ΔN was increased in the lon mutant HA62 from about 3.5 hours to about 7 hours (Table 5). The snoB insertion by itself had no significant effect on the half-life of NifA-ΔN, consistent with the failure of this mutant to increase accumulation of NifA-ΔN or NifA-AUG1. Also in accordance with the results from the Western analysis, NifA-ΔN expressed in a snoB lon double mutant showed an increase in half-life that was greater than the effect of the lon mutation alone, to about 21 hours (Table 5). The half-life of NifA-ΔN in LC24 (snoC) and in HA64 (lon snoC) could not be accurately assessed because the data were more widely scattered for these two strains (FIG. 11; Table 5).

TABLE 5

| Half-life of Nifa-ΔN in MC1061 and sno Mutants at 28° C. | | |
|---|---|---|
| Strain | Half-life (hours)* | Range** |
| MC1061 | 3.5 | 2.7–5.0 |
| HA62 (lon) | 7.0 | 5.4–10.0 |
| LC23 (snoB) | 5.3 | 4.8–5.9 |
| LC24 (snoC) | 5.0 | 2.8–24.5* |
| HA63 (lon snoB) | 21.4 | 12.6–70.2 |
| HA64 (lon snoC) | 3.8 | 2.3–10.3* |

Figure 5:
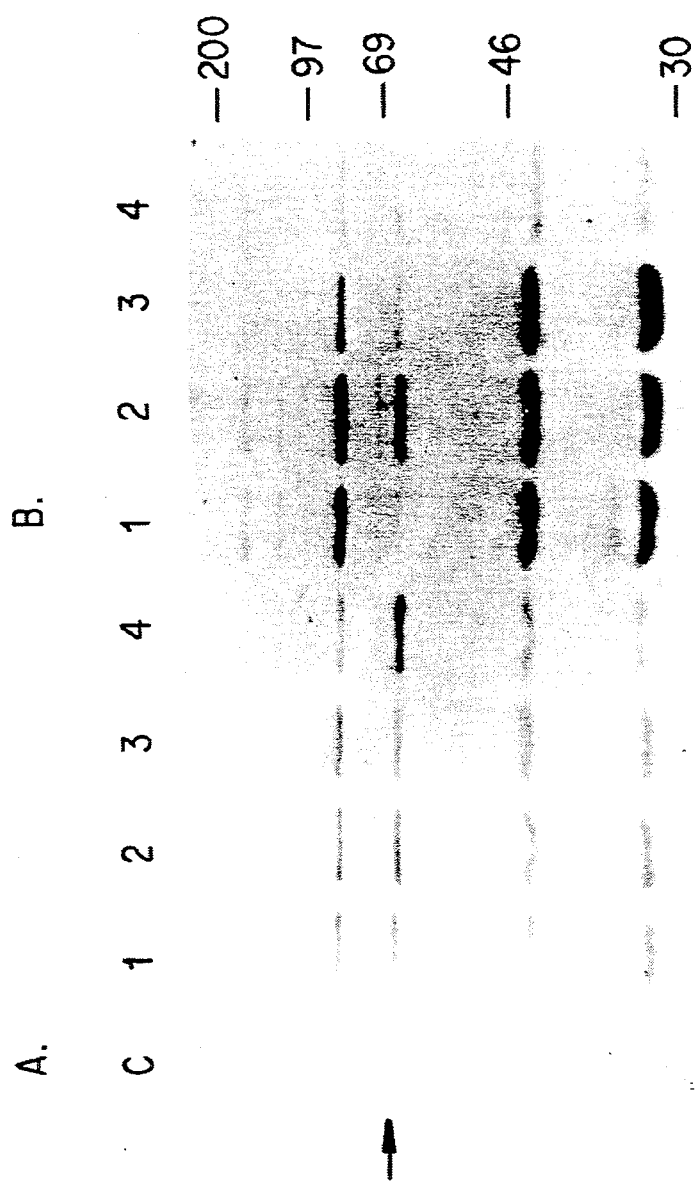
FIG. 5. Immunodetection of R. meliloti NifA-AUG1 in MC1061 and mutant derivatives grown under 1% or 21oxygen. (A) Cells grown under 1% oxygen. Lane C, MC1061 containing only vector (no NifA); lane 1, MC1061 with pEH32 (NifA-AUG1); lane 2, HA62 (lon) with pEH32; lane 3, LC23 (snoB) with pEH32; lane 4, LC24 (snoC) with pEH32. (B) Cells grown under 21% oxygen, lanes as in part A. Positions of molecular weight markers are shown on the right (×0.001).

*Data are for pulse-chase experiment shown in FIG. 5.
**Range given represents the 95% confidence level (two standard deviations). Half-lives were calculated by a least squares fit to an exponential decay curve for a single experiment. Range represents one standard deviation from the mean slope. Another experiment produced similar results (not shown).

Discussion

Previous results have shown that inactivation of NifA at high oxygen levels in E. coli and R. meliloti is not due solely to proteolysis, since for some mutant forms of NifA the level of NifA in the cell declines only slightly as oxygen is increased, while NifA activity decreases much more rapidly (Huala, E. et al., J. Bacteriol. 171:3354–3365 (1989)). The observation that lon and snoC mutants can cause a decline in NifA activity by decreasing the amount of NifA present in the cell can be explained in two ways. One obvious possibility is that the lon and snoC gene products degrade only active NifA or both active and inactive with NifA. Another possibility is that lon and snoC degrade only inactive NifA and affect the level of active NifA only indirectly by eliminating the pool of inactive NifA and consequently preventing the reversal of NifA inactivation. This could be the case if the inactivation of NifA is a reversible reaction. However, since the inactivation of NifA from Bradhyrhizobium japonicum is irreversible (Kullik, I. et al., Arch. Microbiol, 151:191–197 (1989)), this is unlikely to be correct.

E. coli containing both the lon and snoC mutations shows no additional increase in NifA accumulation or half-life when compared with a strain containing only a lon mutation. If the products of the lon and snoC genes were independent proteases, each capable of degrading NifA in the absence of the other, the effects of the two mutations should be additive. Since this is not the case, the products of the lon and snoC genes must work cooperatively to degrade NifA. The idea that the lon product may require another E. coli factor to degrade some proteins has been previously suggested (Schoemaker, J. M. et al., J. Bacteriol. 158:551–561 (1984)). SulA, an unstable regulator of cell division, shows greatly increased stability in a lon mutant. However, the lon gene product by itself may not be sufficient for proteolysis of SulA. Lon is incapable of degrading SulA in vitro, although under the same conditions protein A and casein are degraded, leading to the speculation that other factors may be required for degradation of SulA by Lon.

The snoB gene is unlikely to encode a protease since a mutation in snoB increases NifA activity tenfold without causing a visible increase in NifA accumulation, while a lon or snoC mutant, in order to bring about a similar increase in NifA activity, increases NifA accumulation severalfold. Therefore, the effect of the snoB mutation is on the specific activity of NifA, rather than its accumulation. The decline in NifA activity without a concomitant decline in NifA accumulation with increasing oxygen (Huala, E. et al., *J. Bacteriol.* 171:3354-3365 (1989); see also Table 3) confirms that inactivation of NifA can occur by a mechanism other than degradation. Inactivation by NifA by oxygen has been proposed to occur through a change in the oxidation state of a bound metal ion (Fischer, H.-M. et al., *Nucleic Acids Res.* 16:2207-2224 (1988)). This model for NifA inactivation by oxygen does not immediately suggest the involvement of host factors in the process. However, it is possible that insertions in snoB could indirectly protect NifA from oxidative damage, for example by causing an increase the level of enzymes such as superoxide dismutase and catalase which protect the cell from oxidative damage. Alternatively, the snoB product could act directly to decrease NifA activity in the presence of oxygen, suggesting a role as a functional analogue of *Klebsiella pneumoniae* NifL.

All references cited herein are fully incorporated by reference. Having now fully described the invention, it will be understood by those with skill in the art that the scope may be performed within a wide and equivalent range of conditions, parameters and the like, without affecting the spirit or scope of the invention or any embodiment thereof.

What is claimed is:

1. An *E. coli* bacterial host, wherein said host possesses a mutation in snoC, and wherein said mutation results in a decreased rate of degradation of recombinantly-produced NifA.

2. The host of claim 1, wherein said mutation in snoC is a mutation in the region of 23 to 31 minutes on the *E. coli* genetic map, and wherein said mutation is approximately 10 kilobases away from nirR in the direction of rac.

3. The host of claim 1, wherein said host is ATCC accession number 55040.

4. An *E. coli* bacterial host, wherein said host possesses a mutation in lon and a mutation in snoB, and wherein said mutation results in a decreased rate of degradation of recombinantly-produced NifA.

5. The host of claim 4, wherein said mutation in snoB is located approximately 160 base pairs downstream of the termination codon for alaS.

6. The host of claim 4, wherein said host is ATCC accession number 55040.

7. Purified snoC DNA, wherein said snoC DNA is purified from any of the hosts of claims 1-3.

8. Purified snoB DNA, wherein said snoB DNA is purified from any of the hosts of claims 4-6.

9. The host of any of claims 1 or 4, wherein said NifA is encoded by the *Rhizobium meliloti* NifA gene.

* * * * *

UNITED STATES PATENT AND TRADEMARK OFFICE
CERTIFICATE OF CORRECTION

PATENT NO. : 5,143,846
DATED : September 1, 1992
INVENTOR(S) : Huala et al.

It is certified that error appears in the above-indentified patent and that said Letters Patent is hereby corrected as shown below:

In column 6, line 15, delete "snoB" and replace therewith --snoC--.

In column 6, line 17, delete "snoC" and replace therewith --snoB--.

In column 15, line 61, delete "snoB" and replace therewith --snoC--.

In column 15, line 62, delete "snoC" and replace therewith --snoB--.

Signed and Sealed this

Twenty-ninth Day of March, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,143,846
DATED : September 1, 1992
INVENTOR(S) : Eva Huala, et al

It is certified that error appears in the above-indentified patent and that said Letters Patent is hereby corrected as shown below:

Column 24, line 27, change "55040" to read -- 55039 --.

Signed and Sealed this

Twenty-fifth Day of February, 1997

Attest:

BRUCE LEHMAN

Attesting Officer     Commissioner of Patents and Trademarks